United States Patent
Singh et al.

(10) Patent No.: US 10,905,061 B2
(45) Date of Patent: Feb. 2, 2021

(54) MADS-BOX DOMAIN ALLELES FOR CONTROLLING SHELL PHENOTYPE IN PALM

(71) Applicant: Malaysian Palm Oil Board, Selangor (MY)

(72) Inventors: Rajinder Singh, Kuala Lumpur (MY); Leslie Low Eng Ti, Kuala Lumpur (MY); Leslie Ooi Cheng Li, Kuala Lumpur (MY); Meilina Ong Abdullah, Seremban (MY); Rajanaidu Nookiah, Kuala Lumpur (MY); Ravigadevi Sambanthamurthi, Selangor (MY); Andrew Van Brunt, St. Louis, MO (US); Muhammad A. Budiman, St. Louis, MO (US); Steven W. Smith, Fitchburg, WI (US); Nathan D. Lakey, Chesterfield, MO (US); Rob Martienssen, Cold Spring Harbor, NY (US); Jared Ordway, St. Louis, MO (US)

(73) Assignee: Malaysian Palm Oil Board, Selangor (MY)

( * ) Notice: Subject to any disclaimer, the term of this patent is extended or adjusted under 35 U.S.C. 154(b) by 158 days.

(21) Appl. No.: 15/580,645

(22) PCT Filed: Jun. 14, 2016

(86) PCT No.: PCT/US2016/037429
§ 371 (c)(1),
(2) Date: Dec. 7, 2017

(87) PCT Pub. No.: WO2016/205240
PCT Pub. Date: Dec. 22, 2016

(65) Prior Publication Data
US 2018/0160639 A1    Jun. 14, 2018

Related U.S. Application Data

(60) Provisional application No. 62/180,042, filed on Jun. 15, 2015.

(51) Int. Cl.
| | |
|---|---|
| *A01H 1/04* | (2006.01) |
| *C12Q 1/6895* | (2018.01) |
| *A01H 5/08* | (2018.01) |
| *C07K 14/415* | (2006.01) |
| *C12N 15/82* | (2006.01) |
| *A01H 5/10* | (2018.01) |

(52) U.S. Cl.
CPC ............ *A01H 1/04* (2013.01); *A01H 5/08* (2013.01); *A01H 5/10* (2013.01); *C07K 14/415* (2013.01); *C12N 15/8261* (2013.01); *C12Q 1/6895* (2013.01); *C12Q 2600/13* (2013.01); *C12Q 2600/156* (2013.01); *Y02A 40/146* (2018.01)

(58) Field of Classification Search
None
See application file for complete search history.

(56) References Cited

U.S. PATENT DOCUMENTS

| | | | |
|---|---|---|---|
| 2010/0286068 A1 | 11/2010 | Abdullah et al. | |
| 2013/0247249 A1* | 9/2013 | Singh ................ | C12N 15/8261 800/290 |
| 2015/0024388 A1 | 1/2015 | Singh et al. | |

FOREIGN PATENT DOCUMENTS

WO      2015010008 A1      1/2015

OTHER PUBLICATIONS

Barcelos et al. (Aug. 2002, "Genetic Diversity and Relationship in American and African Oil Palm as Revealed by RFLP and AFLP Molecular Markers", Pesquisa Agropecuaria Brasília, 37(8):1105-1114).*
Extended European Search Report from EP Application No. 16812254 completed on Oct. 12, 2018.
Billotte, N., et al., "Microsatellite-Based High Density Linkage Map in Oil Palm (*Elaeis guineensis* Jacq.)" Theor Appl Genet (2005) 110: 754-765.
Mayes, S, et al., "Construction of a RFLP Genetic Linkage Map for Oil Palm (*Elaeis guineensis* Jacq.)" Genome, vol. 40, 1997, pp. 116-122.
Singh, R., et al., "Development of Simple Sequence Repeat (SSR) Markers for Oil Palm and Their Application in Genetic Mapping and Fingerprinting of Tissue Culture Clones" Asia Pacific Journal of Molecular Biology and Biotechnology, 2007, vol. 15 (3):pp. 121-131.
PCT/US2016/037429 , "International Search Report and Written Opinion", dated Mar. 13, 2017, 17 pages.
Singh et al., "The oil palm Shell gene controls oil yield and encodes a homologue of SEEDSTICK", Nature, Aug. 15, 2013, 500(7462):340-344.
CONC2018/0000194 , "Office Action", dated Jan. 15, 2018, 2 pages.
CONC2018/0000194 , "Office Action", dated Feb. 26, 2020, 9 pages.
IDP00201708995 , "Substantive Examination Report", dated Jan. 17, 2020, 5 pages.

* cited by examiner

*Primary Examiner* — Stuart F Baum
(74) *Attorney, Agent, or Firm* — Kilpatrick Townsend & Stockton LLP

(57) ABSTRACT

Nucleic acid and polypeptide sequences for predicting and controlling shell phenotype in palm.

18 Claims, 3 Drawing Sheets
Specification includes a Sequence Listing.

MADS-BOX DOMAIN ALLELES FOR CONTROLLING SHELL PHENOTYPE IN PALM

CROSS-REFERENCES TO RELATED APPLICATIONS

This application is a U.S. National Stage Entry under 35 U.S.C. § 371 of PCT International Application No. PCT/US2016/037429, filed Jun. 14, 2016, which claims priority to U.S. Provisional Application No. 62/180,042, filed Jun. 15, 2015, the contents of which are hereby incorporated by reference in its entirety for all purposes.

REFERENCE TO SEQUENCE LISTING

This application includes a Sequence Listing as a text file named "096380-1068853-000610US-SEQLIST.txt" created Dec. 6, 2017, and containing 4,456,586 bytes. The material contained in this text file is incorporated by reference in its entirety for all purposes.

BACKGROUND OF THE INVENTION

The oil palm (*E. guineensis* and *E. oleifera*) can be classified into separate groups based on its fruit characteristics, and has three naturally occurring fruit types which vary in shell thickness and oil yield. *Dura* type palms are homozygous for a wild type allele of the shell gene ($sh^+/sh^+$), have a thick seed coat or shell (2-8 mm) and produce approximately 5.3 tons of oil per hectare per year. *Tenera* type palms are heterozygous for a wild type and mutant allele of the shell gene ($sh^+/sh^-$), have a relatively thin shell surrounded by a distinct fiber ring, and produce approximately 7.4 tons of oil per hectare per year. Finally, *pisifera* type palms are homozygous for a mutant allele of the shell gene ($sh^-/sh^-$), have no seed coat or shell, and are usually female sterile (Hartley, 1988) (Table 1). Therefore, the inheritance of the single gene controlling shell phenotype is a major contributor to palm oil yield.

*Tenera* palms are hybrids between the *dura* and *pisifera* palms. Whitmore (1973) described the various fruit forms as different varieties of oil palm. However, Latiff (2000) was in agreement with Purseglove (1972) that varieties or cultivars as proposed by Whitmore (1973), do not occur in the strict sense in this species. As such, Latiff (2000) proposed the term "race" to differentiate *dura*, *pisifera* and *tenera*. Race was considered an appropriate term as it reflects a permanent microspecies, where the different races are capable of exchanging genes with one another, which has been adequately demonstrated in the different fruit forms observed in oil palm (Latiff, 2000). In fact, the characteristics of the three different races turn out to be controlled simply by the inheritance of a single gene. Genetic studies revealed that the shell gene shows co-dominant monogenic inheritance, which is exploitable in breeding programmes (Beirnaert and Vanderweyen, 1941).

The shell gene responsible for this phenotype was first reported in the Belgian Congo in the 1940's (Beirnaert and Venderweyan, 1941). However, *tenera* fruit forms were recognized and exploited in Africa well before then (Devuyst, 1953; Godding, 1930; Sousa et al., 2011). Given the central role played by the shell gene, oil palm breeding utilizes reciprocal recurrent selection of maternal (*dura*) and paternal (*pisifera*) pools using the North Carolina Model 1 maize breeding design (Rajanaidu et al., 2000). The Deli *dura* population, direct descendants of the four original African palms planted in Bogor Botanical Garden, Indonesia (1848), has excellent combining ability with the AVROS (Algemene Vereniging van Rubberplanters ter Oostkust van Sumatra) and other *pisifera* parental palms. AVROS *pisifera* palms were derived from the famous "Djongo" palm from Congo, but more recently several different accessions of *dura* and *pisifera* have also been sourced from Africa (Rajanaidu et al., 2000).

*Tenera* fruit types have a higher mesocarp to fruit ratio, which directly translates to significantly higher oil yield than either the *dura* or *pisifera* palm (as illustrated in Table 1).

TABLE 1

Comparison of dura, tenera and *pisifera* fruit forms

| | Fruit Form | | |
|---|---|---|---|
| Characteristic | Dura | Tenera | Pisifera* |
| Shell thickness (mm) | 2-8 | 0.5-3 | Absence of shell |
| Fibre Ring ** | Absent | Present | Absent |
| Mesocarp Content (% fruit weight) | 35-55 | 60-96 | 95 |
| Kernel Content (% fruit weight) | 7-20 | 3-15 | 3-5 |
| Oil to Bunch (%) | 16 | 26 | — |
| Oil Yield (t/ha/yr) | 5.3 | 7.4 | — |

*usually female sterile, bunches rot prematurely
** fibre ring is present in the mesocarp and often used as diagnostic tool to differentiate dura and tenera palms.
(Source: Hardon et al., 1985; Hartley, 1988)

Since the crux of the breeding programmes in oil palm is to produce planting materials with higher oil yield, the *tenera* palm is the preferred choice for commercial planting. It is for this reason that substantial resources are invested by commercial seed producers to cross selected *dura* and *pisifera* palms in hybrid seed production. And despite the many advances which have been made in the production of hybrid oil palm seeds, two significant problems remain in the seed production process. First, batches of *tenera* seeds, which will produce the high oil yield *tenera* type palm, are often contaminated with *dura* seeds (Donough and Law, 1995). Today, it is estimated that *dura* contamination of *tenera* seeds can reach rates of approximately 5% (reduced from as high as 20-30% in the early 1990's as the result of improved quality control practices). Seed contamination is due in part to the difficulties of producing pure *tenera* seeds in open plantation conditions, where workers use ladders to manually pollinate tall trees, and where palm flowers for a given bunch mature over a period time, making it difficult to pollinate all flowers in a bunch with a single manual pollination event. Some flowers of the bunch may have matured prior to manual pollination and therefore may have had the opportunity to be wind pollinated from an unknown tree, thereby producing contaminant seeds in the bunch. Alternatively premature flowers may exist in the bunch at the time of manual pollination, and may mature after the pollination occurred allowing them to be wind pollinated from an unknown tree thereby producing contaminant seeds in the bunch. Prior to the invention described herein, it was not possible to identify the fruit type of a given seed or a given plant arising from a seed until the plant matured enough to produce a first batch of fruit, which typically takes approximately six years after germination. Notably, in the four to five years interval from germination to fruit production, significant land, labor, financial and energy resources are invested into what are believed to be *tenera* trees, some of which will ultimately be of the unwanted low yielding contaminant fruit types. By the time these suboptimal trees are identified, it is impractical to remove them from the field and replace them with *tenera* trees, and thus growers achieve lower palm oil yields for the 25 to 30 year production life of the contaminant trees. Therefore, the issue of contamination of batches of *tenera* seeds with *dura* or *pisifera* seeds is a problem for oil palm breeding, underscoring the need for a method to predict the fruit type of seeds and nursery plantlets with high accuracy.

A second problem in the seed production process is the investment seed producers make in maintaining *dura* and *pisifera* lines, and in the other expenses incurred in the hybrid seed production process. Traditionally, there was no know way to produce a tree with an optimal shell phenotype which when crossed to itself or to another tree with optimal shell phenotype would produce seeds which would only generate optimal shell phenotypes. Therefore, there is a need to engineer trees to breed true from one generation to the next for optimal shell phenotype. There is also a need to separate predicted *tenera* plants (e.g., seeds or seedlings) from any contaminating *dura* and/or *pisifera* plants produced during the the hybrid production process. Similarly, there is a need to separate predicted *dura* plants from *pisifera* and/or *tenera* plants and predicted *pisifera* plants from *dura* and/or *tenera* plants to maintain breeding stocks for hybrid production.

The genetic mapping of the SHELL gene was initially attempted by Mayes et al. (1997). A second group in Brazil, using a combination of bulked segregation analysis (BSA) and genetic mapping, reported two random amplified polymorphic DNA (RAPD) markers flanking the shell locus (Moretzsohn et al., 2000). More recently, Billotte et al., (2005) reported a simple sequence repeat (SSR)-based high density linkage map for oil palm, involving a cross between a thin shelled *E. guineensis* (*tenera*) palm and a thick shelled *E. guineensis* (*dura*) palm. A patent application filed by the Malaysian Palm Oil Board (MPOB) describes the identification of a marker using restriction fragment technology, in particular a Restriction Fragment Length Polymorphism (RFLP) marker linked to the shell gene for plant identification and breeding purposes (RAJINDER SINGH, LESLIE OOI CHENG-LI, RAHIMAH A. RAHMAN AND LESLIE LOW ENG TI. 2008. Method for identification of a molecular marker linked to the shell gene of oil palm. Patent Application No. PI 20084563. Patent Filed on 13 Nov. 2008). The RFLP marker (SFB 83) was identified by way of generation or construction of a genetic map for a *tenera* fruit type palm. The patent application publications U.S. 2013/024729 and U.S. 2015/0037793, filed by MPOB, describe the identification of the SHELL gene, two *pisifera* alleles ($sh^{AVROS}$ and $sh^{MPOB}$) and methods for predicting fruit form phenotype by detecting wild-type and *pisifera* alleles of the SHELL gene.

BRIEF SUMMARY OF THE INVENTION

Here we describe the identification of novel alleles of the SHELL gene responsible for different fruit form phenotypes and methods for predicting or determining the shell phenotype of a palm plant (including but not limited to a whole palm plant or palm seed). The SHELL gene is an oil palm MADS-box gene substantially similar to *Arabidopsis* SEEDSTICK (STK), also referred to as AGAMOUS-like 11 (AGL11), as well as to *Arabidopsis* SHATTERPROOF (SHP1), also referred to as AGAMOUS-like 1 (AGL1).

Two SHELL alleles, $sh^{MPOB}$ and $sh^{AVROS}$, have been previously identified either of which result in the preferred *tenera* fruit form when present in an oil palm having one copy of a mutant allele and one wild-type allele. For example, heterozygous oil palms including the wildtype SHELL allele, $Sh^{DeliDura}$, on one chromosome and either of the two mutant SHELL alleles on the other chromosome exhibit a *tenera* phenotype.

Described herein are nine additional mutations in exon one of the SHELL gene, referred to as SHELL alleles three (3), four (4), five (5), six (6), seven (7), eight (8), nine (9), ten (10), and eleven (11). The amino acid sequences of the SHELL gene product resulting from alleles 3-11 are depicted in SEQ ID NOs:3-11 respectively. The nucleotide sequences for exon 1 of the SHELL gene for alleles 3-11 are depicted in SEQ ID NOs:13-21 respectively. As with the $sh^{MPOB}$ and $sh^{AVROS}$ alleles, the presence of these SHELL alleles can result in a *tenera* phenotype when heterozygous with a wild-type allele or a *pisifera* phenotype when either homozygous, or heterozygous with another non-functional SHELL allele.

In reference to the wild-type SHELL ($Sh^{DeliDura}$) gene, the allele 3 polymorphism is an adenosine to cytosine (A→C) mutation at nucleotide position 67 of exon 1 of the SHELL gene. Allele 3 results in a lysine to glutamine substitution within the conserved MADS box domain of SHELL. As diagrammed in FIG. 1, the entire MADS box domain of SHELL is encoded by exon 1 of the SHELL gene. The variant amino acid occurs 6 amino acids N-terminal to the amino acid substitution arising from the $sh^{MPOB}$ allele, 8 amino acids N-terminal to the amino acid substitution arising from the $sh^{AVROS}$ allele, and at position 23 of the translated open reading frame of exon 1 (FIGS. 2 and 3).

Similarly, the allele 4 polymorphism is a cytosine to adenosine (C→A) mutation at nucleotide position 122 of exon 1 of the SHELL gene. Allele 4 results in an alanine to aspartate substitution within the conserved MADS box domain of SHELL. The variant amino acid occurs at position 41 of the translated open reading frame of exon 1 (FIGS. 2 and 3).

The allele 5 polymorphism is an adenosine to thymine (A→T) mutation at nucleotide position 69 of exon 1 of the SHELL gene. Allele 5 results in a lysine to asparagine mutation at position 23 of the translated open reading frame of exon 1 (FIGS. 2 and 3). The allele 6 polymorphism is a guanosine to cytosine (G→C) mutation at position 34 of exon 1 of the SHELL gene. Allele 6 results in a glutamate to glutamine mutation at position 12 of the translated open reading frame of exon 1 (FIGS. 2 and 3). The allele 7 polymorphism is a deletion of fifteen nucleotides at positions 23-37 of exon 1 of the SHELL gene (or nucleotides 22-36 because alignment of the gap is ambiguous). Allele 7 results in an in frame deletion of five amino acids at positions 8 to 12 of the translated open reading frame of exon 1 (FIGS. 2 and 3). Amino acid positions 8 to 12 of the SHELL gene are encoded by nucleotides 22-36. The allele 8 polymorphism is a guanosine to adenosine (G→A) mutation at position 71 of exon 1 of the SHELL gene. Allele 8 results in an arginine to histidine mutation at position 24 of the translated open reading frame of exon 1 (FIGS. 2 and 3).

The allele 9 polymorphism is a cytosine to guanosine (C→G) mutation at position 70 of exon 1 of the SHELL gene. Allele 9 results in an arginine to glycine mutation at position 24 of the translated open reading frame of exon 1. The allele 10 polymorphism is a thymine to adenosine (T→A) mutation at position 110 of exon 1 of the SHELL gene. Allele 10 results in a valine to aspartate mutation at position 37 of the translated open reading frame of exon 1 (FIGS. 2 and 3).

The allele 11 polymorphism is a thymine to cytosine (T→C) mutation at position 114 of exon 1 of the SHELL gene. Allele 11 is a silent mutation in that it does not affect the resulting amino acid sequence of the SHELL gene product (FIGS. 2 and 3). This mutation can be detected to confirm or predict the presence or absence of a wildtype SHELL gene product and therefore predict a *dura* phenotype when homozygous or heterozygous with another wildtype allele in a palm plant and a *tenera* phenotype when heterozygous with an inactive SHELL allele. Alternatively, in some embodiments this mutation can affect gene expression and/or transcriptional or translational regulation of the SHELL gene. Accordingly in such embodiments, the mutation can correlate with a *pisifera* when homozygous or heterozygous with an inactive SHELL allele in a palm plant or *tenera* when heterozygous with a wildtype allele.

Also described herein is a mutation in intron 1 of the SHELL gene that has been discovered in a subset of oil palm plants having the allele 3 mutation. This mutation is referred to herein as allele 12 and depicted in SEQ ID NO:12. The mutation results in deletion of four nucleotides at positions 43-46 of intron 1 of the wild-type SHELL ($Sh^{DeliDura}$) gene. The mutation may be silent in that it may not by itself contribute to the presence or absence of a SHELL fruit form phenotype (e.g., *dura, tenera,* or *pisifera*). However, due to the close physical distance (i.e., genetic linkage) between the intron 1 mutation and exon 1, the contribution of parental germ plasm known to have a particular SHELL allele (wild-type or mutant) within exon 1 and the intron 1 marker can be tracked with a high degree of confidence in progeny by detection of the allele 12 mutation rather than a mutation in exon 1. Moreover, in some cases, the mutation in intron 1 may be in linkage disequilibrium with exon 1 or a portion thereof. Alternatively, allele 12 may alter transcriptional regulation or splicing and thus exhibit a *pisifera* SHELL phenotype when homozygous or a *tenera* phenotype when heterozygous with a wildtype SHELL allele.

Nuclear proteins, such as transcription factors, must be actively transported into and retained within the nucleus to be functional. The nuclear localization mechanism involves the binding of nuclear localization protein signals in the nuclear protein to importin α and importin β subunits in the cytoplasm. Importin α binds to the nuclear localization signal (NLS), while importin β interacts with importin α as well as the nuclear pore. In plant MADS box proteins, the prominent NLS amino acid motif is KR[K or R]X₄KK (SEQ ID NO:29), where X can be any amino acid (Gramzow and Theissen, 2010). The SHELL MADS box domain includes this motif (KRRNGLLKK; SEQ ID NO:30) at amino acids 23-31. MADS box proteins may also have a bipartite NLS which that involves additional upstream amino acids. An example is the bipartite NLS of *petunia* FLORAL BINDING PROTEIN 11 (FBP11) which includes the sequence MGRGKIEIKRIENNTNRQVTFCKRRNGLLKK (SEQ ID NO:31). The bipartite NLS is made up of NLS amino acids (underlined), as well as conserved basic amino acids (italicized), all of which contribute to the nuclear localization mechanism (Immink et al., 2002).

The SHELL MADS box domain includes a very similar bipartite NLS including amino acids 3, 5, 9-10, and 21-31 (MGRGKIEIKRIENTTSRQVTFCKRRNGLLKK; SEQ ID NO:32) (FIGS. 2 and 3). It is noteworthy that of the ten sequence changes resulting in amino acid substitutions or deletions reported here ($sh^{AVROS}$, $sh^{MPOB}$, and alleles 3-10), six change one or more of these highly conserved NLS amino acids ($sh^{AVROS}$, shMPOB, allele 3, allele 5, allele 7, allele 8 and allele 9), and a 7$^{th}$ ($sh^{MPOB}$) introduces a proline substitution at a variable position within the prominent NLS that would be expected to significantly alter the secondary structure of the protein within the NLS domain (FIGS. 2 and 3). These findings suggest that a common mechanism imparting the *pisifera* (when homozygous or heterozygous with another nonfunctional SHELL allele) or *tenera* (when heterozygous with a wildtype SHELL allele) phenotype may be the reduction or prevention of the nuclear localization of nonfunctional SHELL proteins or dimers of SHELL proteins with other MADS box transcription factors. Therefore, it is likely that mutation of any of the conserved NLS amino acids (boxed in FIGS. 2 and 3), or any mutation that disrupted SHELL NLS function, can be associated with the *pisifera* or *tenera* phenotype.

Accordingly in one aspect, methods for determining or predicting the shell phenotype of a palm (e.g., oil palm) plant (including but not limited to a whole palm plant or palm seed) are provided. In some embodiments, the method comprises, providing a sample from the plant or seed; and determining from the sample the genotype of a polymorphic marker at a position in exon 1 of the SHELL gene selected from the group consisting of nucleotides:

(i) 7, 8, 9, 13, 14, 15, 22, 23, 24, 25, 26, 27, 28, 29, 30, 31, 32, 33, 34, 35, 36, 37, 61, 62, 63, 64, 65, 66, 67, 68, 69, 70, 71, 72, 73, 74, 75, 76, 77, 78, 79, 80, 81, 82, 83, 84, 85, 87, 88, 89, 90, 91, 92, 109, 110, 111, 114, 121, 122, and 123;

(ii) 23, 24, 25, 26, 27, 28, 29, 30, 31, 32, 33, 34, 35, 36, 37, 67, 69, 70, 71, 110, 114, and 122; or (iii) 7-9, 13-15, 25-30, 61-75 and 88-92. In some cases, heterozygosity at one or more of the polymorphic markers for a *pisifera* and a *dura* allele predicts the presence of the *tenera* shell phenotype. In some cases, homozygosity for a genotype of a predicted *pisifera* allele at one or more of the polymorphic markers predicts the presence of the *pisifera* shell phenotype. In some cases, the genotype of the polymorphic marker can comprise one or more of the predicted *pisifera* allele genotypes depicted in SEQ ID NOs: 13-21.

In some cases, a mutation with respect to the wild-type SHELL ($Sh^{DeliDura}$) gene at one or more of the nucleotide positions that results in an amino acid substitution (e.g., non-conservative substitution), deletion, insertion, or frameshift can predict a *pisifera* phenotype when homozygous or heterozygous with a different mutation with respect to the wild-type SHELL ($Sh^{DeliDura}$) gene, or a *tenera* phenotype when heterozygous with respect to the wild-type allele. For example, a mutation with respect to the wild-type SHELL ($Sh^{DeliDura}$) gene at one or more of the nucleotide positions that results in an amino acid substitution (e.g., non-conservative substitution), deletion, insertion, or frameshift can predict a *pisifera* phenotype when heterozygous with a different mutation that results in a non-functional SHELL gene, such as a mutation that results in a different substitution (e.g., non-conservative substitution), deletion, insertion, or frameshift.

In some embodiments, the genotype of the polymorphic marker comprises a deletion or mutation of one or more nucleotides selected from the group consisting of nucleotides: (i) 22, 23, 24, 25, 26, 27, 28, 29, 30, 31, 32, 33, 34, 35, 36, and 37; (ii) 22, 23, 24, 25, 26, 27, 28, 29, 30, 31, 32, 33, 34, 35, and 36; or (iii) 23, 24, 25, 26, 27, 28, 29, 30, 31, 32, 33, 34, 35, 36, and 37, of exon 1 of the SHELL gene. In some embodiments, the genotype of the polymorphic marker comprises a deletion of one or more, or all, of nucleotides 23-37 (or 22-36) of exon 1 of the SHELL gene. In some embodiments, the genotype of the polymorphic marker comprises a mutation of nucleotide 34 of exon 1 of the SHELL gene (e.g., a mutation relative to $Sh^{DeliDura}$). In some embodiments, the mutation comprises a missense (e.g., non-conservative substitution), nonsense, insertion, deletion, or frameshift mutation. In some embodiments, the genotype of the polymorphic marker comprises a cytosine (C) at nucleotide 34 of exon 1 of the SHELL gene.

In some embodiments, the genotype of the polymorphic marker comprises a mutation of nucleotide 67 of exon 1 of the SHELL gene (e.g., a mutation relative to $Sh^{DeliDura}$). In some embodiments, the mutation comprises a missense (e.g., non-conservative substitution), nonsense, insertion, deletion, or frameshift mutation. In some embodiments, the genotype of the polymorphic marker comprises a cytosine (C) at nucleotide 67 of exon 1 of the SHELL gene. In some embodiments, the genotype of the polymorphic marker comprises a mutation of nucleotide 69 of exon 1 of the SHELL gene (e.g., a mutation relative to $Sh^{DeliDura}$). In some embodiments, the mutation comprises a missense (e.g., non-conservative substitution), nonsense, insertion, deletion, or frameshift mutation. In some embodiments, the genotype of the polymorphic marker comprises a thymine (T) at nucleotide 69 of exon 1 of the SHELL gene.

In some embodiments, the genotype of the polymorphic marker comprises a mutation of nucleotide 70 of exon 1 of the SHELL gene (e.g., a mutation relative to $Sh^{DeliDura}$). In some embodiments, the mutation comprises a missense (e.g., non-conservative substitution), nonsense, insertion, deletion, or frameshift mutation. In some embodiments, the genotype of the polymorphic marker comprises a guanosine (G) at nucleotide 70 of exon 1 of the SHELL gene. In some embodiments, the genotype of the polymorphic marker comprises a mutation of nucleotide 71 of exon 1 of the SHELL gene (e.g., a mutation relative to $Sh^{DeliDura}$). In some embodiments, the mutation comprises a missense (e.g., non-conservative substitution), nonsense, insertion, deletion, or frameshift mutation. In some embodiments, the genotype of the polymorphic marker comprises an adenosine (A) at nucleotide 71 of exon 1 of the SHELL gene. In some embodiments, the genotype of the polymorphic marker comprises a mutation of nucleotide 110 of exon 1 of the SHELL gene (e.g., a mutation relative to $Sh^{DeliDura}$). In some embodiments, the mutation comprises a missense (e.g., non-conservative substitution), nonsense, insertion, deletion, or frameshift mutation. In some embodiments, the genotype of the polymorphic marker comprises an adenosine (A) at nucleotide 110 of exon 1 of the SHELL gene.

In some embodiments, the genotype of the polymorphic marker comprises a mutation of nucleotide 114 of exon 1 of the SHELL gene (e.g., a mutation relative to $Sh^{DeliDura}$). In some embodiments, the mutation comprises a missense (e.g., non-conservative substitution), nonsense, insertion, deletion, or frameshift mutation. In some embodiments, the genotype of the polymorphic marker comprises a cytosine (C) at nucleotide 114 of exon 1 of the SHELL gene. In some embodiments, the genotype of the polymorphic marker comprises a mutation of nucleotide 122 of exon 1 of the SHELL gene (e.g., a mutation relative to $Sh^{DeliDura}$). In some embodiments, the mutation comprises a missense (e.g., non-conservative substitution), nonsense, insertion, deletion, or frameshift mutation. In some embodiments, the genotype of the polymorphic marker comprises an adenosine (A) at nucleotide 122 of exon 1 of the SHELL gene.

In any one of the foregoing embodiments, the method can comprise, providing a sample from the plant or seed; and determining from the sample the genotype of a polymorphic marker at a position in exon 1 of the SHELL gene selected from the group consisting of nucleotides:

(i) 22, 23, 24, 25, 26, 27, 28, 29, 30, 31, 32, 33, 34, 35, 36, 37, 67, 68, 69, 70, 71, 72, 73, 74, 75, 76, 77, 78, 79, 80, 81, 82, 83, 84, 85, 87, 88, 89, 90, 91, 92, 110, 114, and 122;

(ii) 23, 24, 25, 26, 27, 28, 29, 30, 31, 32, 33, 34, 35, 36, 37, 67, 69, 70, 71, 110, 114, and 122; or (iii) 67, 69, 70, and 71. In some cases, heterozygosity at one or more of the polymorphic markers for a pisifera and a dura allele predicts the presence of the tenera shell phenotype. In some cases, homozygosity for a genotype of a predicted pisifera allele at one or more of the polymorphic markers predicts the presence of the pisifera shell phenotype. In some cases, heterozygosity for a genotype of a first predicted pisifera allele at one or more of the polymorphic markers and a second predicted pisifera allele at one or more of the polymorphic markers predicts the presence of the pisifera shell phenotype. In some cases, the genotype of the polymorphic marker can comprise one or more of the predicted pisifera allele genotypes depicted in SEQ ID NOs:13, 15, 17, 18, and 19.

In some embodiments, the method comprises, providing a sample from the plant or seed; and determining from the sample the genotype of a polymorphic marker at a position in intron 1 of the SHELL gene selected from the group consisting of nucleotides 43, 44, 45, and 46. In some cases, heterozygosity at one or more of the polymorphic markers for a pisifera and a dura allele predicts the presence of the tenera shell phenotype. In some cases, homozygosity for a genotype of a predicted pisifera allele at one or more of the polymorphic markers predicts the presence of the pisifera shell phenotype. In some cases, heterozygosity for a genotype of a first predicted pisifera allele at one or more of the polymorphic markers and a genotype of a second predicted pisifera allele at one or more of the polymorphic markers predicts the presence of the pisifera shell phenotype. In some cases, the genotype of the polymorphic marker can comprise one or more, or all, of the deleted of the nucleotides of intron 1 depicted in SEQ ID NO:12.

In some embodiments, the method comprises, providing a sample from the plant or seed; and detecting in the sample a genotype of a polymorphic marker that encodes for a mutation in the SHELL gene product at one or more amino acid positions selected from the group consisting of amino acid positions 3, 5, 8, 9, 10, 11, 12, 21, 22, 23, 24, 25, 26, 27, 28, 30, 37, and 4, 1 selected from the group consisting of amino acid positions 3, 5, 8, 9, 10, 11, 12, 21, 22, 23, 24, 25, 26, 27, 28, 30, 31, 37, and 41, selected from the group consisting of amino acid positions 8, 9, 10, 11, 12, 23, 24, 37, and 41 or selected from the group consisting of amino acid positions 8, 9, 10, 11, 12, 23, 24, 31, 37, and 41. In some cases, the genotype of the polymorphic marker comprises a deletion of one or more, or all, of the amino acids at positions 8-12 of the wildtype SHELL gene product. In some cases, heterozygosity at one or more of the polymorphic markers for a pisifera and a dura allele predicts the presence of the tenera shell phenotype. In some cases, homozygosity for a genotype of a predicted pisifera allele at one or more of the polymorphic markers predicts the presence of the pisifera shell phenotype. In some cases, heterozygosity for a genotype of a first predicted pisifera allele at one or more of the polymorphic markers and a second predicted pisifera allele at one or more of the polymorphic markers predicts the presence of the pisifera shell phenotype. In some cases, the genotype of the polymorphic marker can comprise one or more of the predicted pisifera allele SHELL gene products depicted in SEQ ID NOs:3-10, or one or more of the predicted pisifera allele SHELL gene products depicted in SEQ ID NOs:3, 5, 7, 8, and 9.

In some embodiments, the genotype of the polymorphic marker comprises a mutation at amino acid position 23 as compared to the wildtype SHELL gene product. In some cases, the mutation comprises a lysine to glutamine or a lysine to asparagine mutation at amino acid position 23. In some embodiments, the genotype of the polymorphic marker comprises a mutation at amino acid position 24 as compared to the wildtype SHELL gene product. In some cases, the mutation comprises an arginine to histidine or an arginine to glycine mutation at amino acid position 24. In some embodiments, the genotype of the polymorphic maker comprises a mutation at amino acid position 37 of the wildtype SHELL gene product. In some cases, the mutation comprises a valine to aspartate mutation at amino acid 37. In some embodiments, the genotype of the polymorphic marker comprises a mutation at amino acid position 41 of the wildtype SHELL gene product. In some cases, the mutation comprises an alanine to aspartate mutation at amino acid 41.

In some embodiments, the method comprises, providing a sample from the plant or seed; and detecting in the sample a genotype of a polymorphic marker that encodes for a mutation in the SHELL gene product at a position in the nuclear localization signal (NLS) of the SHELL gene product, wherein the mutation at the position in the NLS comprises a mutation at an amino acid position selected from the group consisting of amino acid position 3, 5, 9, 10, 21, 22, 23, 24, 25, 26, 27, 28, and 30; or amino acid position 23, 24, 25, 26, 27, 28, and 30 of the SHELL gene product. In some cases, the mutation is at an amino acid position selected from the group consisting of amino acid position 23 and 24 of the SHELL gene product. In some cases, the mutation at amino acid position 23 comprises a lysine to glutamine mutation. In some cases, the mutation at amino acid position 23 comprises a lysine to asparagine mutation. In some cases, the mutation at amino acid position 24 comprises an arginine to histidine mutation. In some cases, the mutation at amino acid position 24 comprises an arginine to glycine mutation.

In some embodiments, the plant or seed is generated from i) a cross between a plant having the *dura* shell phenotype and a plant having the *pisifera* shell phenotype, ii) the selfing of a *tenera* palm, iii) a cross between two plants having the *tenera* shell phenotype, iv) a cross between a plant having the *dura* shell phenotype and a plant having the *tenera* shell phenotype, or v) a cross between a plant having the *tenera* shell phenotype and a plant having the *pisifera* shell phenotype. In some embodiments, the plant is less than 5 years old. In some embodiments, the plant is less than one year old. In some embodiments, the polymorphic marker is, or is at least, 86, 88, 90, 92, 94, 96, 97, 98, or 99% predictive of the *tenera* phenotype.

In some embodiments, the method further comprises selecting the seed or plant for cultivation if the plant is heterozygous for the polymorphic marker (e.g., heterozygous for a *dura* and a *pisifera* marker predicting a *tenera* phenotype). In some embodiments, the method further comprises selecting the seed or plant for cultivation if the plant is homozygous for a polymorphic marker (e.g., indicating a *dura* or a *pisifera* phenotype). In some embodiments, plants or seeds are discarded, stored (e.g., stored separately from *tenera* plants or seeds) or cultivated (e.g., cultivated separately from *tenera* plants or seeds) if the plants or seeds do not have a genotype predictive of the *tenera* shell phenotype, such as if the plants or seeds have a genotype predictive of a *pisifera* phenotype or have a genotype predictive of a *dura* phenotype.

Also provided is a method for segregating a plurality of palm (e.g., oil palm) plants into different categories based on predicted shell phenotype. In some embodiments, the method comprises, providing a sample from each plant in the plurality of plants; determining from the samples the genotype of at least one polymorphic marker at a position in exon 1 of the SHELL gene selected from the group consisting of: (i) nucleotides 7, 8, 9, 13, 14, 15, 22, 23, 24, 25, 26, 27, 28, 29, 30, 31, 32, 33, 34, 35, 36, 37, 61, 62, 63, 64, 65, 66, 67, 68, 69, 70, 71, 72, 73, 74, 75, 76, 77, 78, 79, 80, 81, 82, 83, 84, 85, 87, 88, 89, 90, 91, 92, 109, 110, 111, 114, 121, 122, and 123; (ii) nucleotides 23, 24, 25, 26, 27, 28, 29, 30, 31, 32, 33, 34, 35, 36, and 37; (iii) nucleotide 34; (iv) nucleotides 67, 68, 69, 70, 71, 72, 73, 74, 75, 76, 77, 78, 79, 80, 81, 82, 83, 84, 85, 87, 88, 89, 90, 91, and 92; (v) nucleotides 67, 69, 70, and 71; (vi) nucleotide 67; (vii) nucleotide 69; (viii) nucleotide 70; (ix) nucleotide 71; (x) nucleotide 110; (xi) nucleotide 114; or (xii) nucleotide 122; and segregating the plants into groups based on the genotype of the polymorphic marker, wherein the groups correspond to plants predicted to have the *tenera* shell phenotype, plants predicted to have the *dura* shell phenotype, and plants predicted to have the *pisifera* shell phenotype.

Also provided are kits for determining the shell phenotype of a palm seed or plant. In some embodiments, the kit comprises, one or more oligonucleotide primers or probes that independently comprise:

a sequence of at least, e.g., 6, 7, 8, 9, 10, 11, 12, 13, 14, 15, 16, 17, or 18 (or 20, 22, 24, 30, or more) consecutive nucleotides of SEQ ID NO:27; or;

a sequence 100% complementary to at least e.g., 6, 7, 8, 9, 10, 11, 12, 13, 14, 15, 16, 17, or 18 (or 20, 22, 24, 30, or more) consecutive nucleotides of SEQ ID NO:27, wherein the one or more primers or probes independently hybridize to a sequence that is within, or within about, 5,000; 2,500; 1,000; 750; 500; 250; 200; 150; 100; 75; 50; 25, or 1 bp of a position in exon 1 of the SHELL gene selected from the group consisting of:

(i) nucleotides 7, 8, 9, 13, 14, 15, 22, 23, 24, 25, 26, 27, 28, 29, 30, 31, 32, 33, 34, 35, 36, 37, 61, 62, 63, 64, 65, 66, 67, 68, 69, 70, 71, 72, 73, 74, 75, 76, 77, 78, 79, 80, 81, 82, 83, 84, 85, 87, 88, 89, 90, 91, 92, 109, 110, 111, 114, 121, 122, and 123;

(ii) nucleotides 23, 24, 25, 26, 27, 28, 29, 30, 31, 32, 33, 34, 35, 36, and 37;

(iii) nucleotide 34;

(iv) nucleotides 67, 68, 69, 70, 71, 72, 73, 74, 75, 76, 77, 78, 79, 80, 81, 82, 83, 84, 85, 87, 88, 89, 90, 91, and 92

(v) nucleotides 67, 69, 70, and 71;

(vi) nucleotide 67;

(vii) nucleotide 69;

(viii) nucleotide 70;

(ix) nucleotide 71;

(x) nucleotide 110;

(xi) nucleotide 114; or (xii) nucleotide 122.

In some embodiments, the one or more primers or probes independently hybridize to a sequence that is adjacent to, or contains, a position in exon 1 of the SHELL gene selected from the group consisting of one or more of the foregoing groups of nucleotides (i)-(xii).

In some embodiments, the one or more primers or probes specifically hybridize to palm plant DNA or RNA.

In some embodiments, a detectable label is linked (e.g., covalently linked) to the oligonucleotide. In some embodiments, the detectable label is fluorescent.

In some embodiments, the kit further comprises a polynucleotide encoding a polypeptide comprising a sequence substantially (e.g., a least 80, 85, 90, 95, 97, 98, 99%) identical or identical to at least 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive nucleotides of SEQ ID NO: 13, 14, 15, 16, 17, 18, 19, 20, or 21, wherein the polynucleotide comprises a mutation depicted in SEQ ID NO:13, 14, 15, 16, 17, 18, 19, 20, or 21 relative to wild-type, $sh^{AVROS}$, or $sh^{MPOB}$ SHELL.

Also provided is an isolated nucleic acid comprising a polynucleotide encoding a polypeptide comprising a sequence substantially (e.g., a least 80, 85, 90, 95, 97, 98, 99%) identical or identical to at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive amino acids of SEQ ID NO:3, 4, 5, 6, 7, 8, 9, 10, or 11, wherein the polynucleotide comprises a mutation depicted in SEQ ID NO:13, 14, 15, 16, 17, 18, 19, 20, or 21 relative to wild-type, $sh^{AVROS}$, or $sh^{MPOB}$ SHELL.

Also provided is a cell or seed or plant comprising a heterologous expression cassette, the expression cassette comprising a heterologous promoter operably linked to a polynucleotide encoding a polypeptide comprising a sequence substantially (e.g., a least 80, 85, 90, 95, 97, 98, 99%) identical or identical to SEQ ID NO:3, 4, 5, 6, 7, 8, 9, 10, or 11, e.g., wherein the polynucleotide comprises a mutation depicted in SEQ ID NO: 13, 14, 15, 16, 17, 18, 19, 20, or 21 relative to wild-type, $sh^{AVROS}$, or $sh^{MPOB}$ SHELL. In some embodiments, the seed or plant is a palm (e.g., oil palm) seed or palm (e.g., oil palm) plant. In some embodiments, the polypeptide comprises the amino acid sequence of SEQ ID NO:3, 4, 5, 6, 7, 8, 9, 10, or 11. In some embodiments, the heterologous promoter results in expression level of an RNA encoding the polypeptide in the seed or plant that is less than, equal to, or more than expression of an endogenous SHELL RNA in the seed or plant. In some embodiments, the seed or plant comprises two dura alleles of an endogenous SHELL gene. In some embodiments, the seed or plant produces fruit having mature shells that are on average less than 2 mm thick, less than 3 mm thick, or are between 0.5 and 3 mm thick.

Also provided is a cell or seed or plant comprising a heterologous expression cassette, the expression cassette comprising a promoter operably linked to a polynucleotide having at least 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 consecutive nucleotides of SEQ ID NO:13, 14, 15, 16, 17, 18, 19, 20, or 21, or a complement thereof, which polynucleotide, when expressed in the seed or plant, reduces expression of an endogenous SHELL polypeptide in the seed or plant (compared to a control plant lacking the expression cassette), wherein reduced expression of the SHELL polypeptide results in reduced shell thickness of the future seeds produced by the plant. In some embodiments, the polynucleotide encodes an siRNA, antisense polynucleotide, a microRNA, or a sense suppression nucleic acid, thereby suppressing expression of an endogenous SHELL gene. In some embodiments, the seed or plant makes mature shells that are on average less than 2 mm thick, less than about 3 mm thick, or are between 0.5 and 3 mm thick.

Also provided is a method of making a plant as described above or elsewhere herein, comprising introducing the expression cassette into a plant.

Also provided is a method of cultivating the plants described herein.

Other embodiments will be evident from reading the rest of the disclosure.

Definitions

A "shell phenotype" refers to the three fruit forms of E. guineensis-dura, tenera and pisifera. The dura (wild-type) fruit form is exemplified by the presence of a shell having an average thickness of at least 2-8 mm and is typically found in palm plants having a homozygous wild-type SHELL genotype. The pisifera fruit form is exemplified by the absence of a shell and is typically found in palm plants that lack a functional SHELL gene. For example, a pisifera palm plant can have two non-functional SHELL genes (e.g., homozygous for a non-functional SHELL genotype or heterozygous for two different non-functional SHELL genotypes). The tenera fruit form is exemplified by the presence of a thin shell having an average thickness of less than about 3 mm (e.g., approximately 0.5-3 mm) and is typically found in palm plants that are heterozygous for a functional and a non-functional SHELL gene. Heterologous palm plants that overexpress or underexpress the SHELL gene or gene product or partially or completely interfere with the activity of an endogenous SHELL gene product can also exhibit a dura, tenera, or pisifera fruit form phenotype.

A "polymorphic marker" refers to a genetic marker that distinguishes between two alleles. The polymorphic marker can be a nucleotide substitution, insertion, deletion, or rearrangement, or a combination thereof.

As used herein, "detecting a genotype" refers to: (i) analyzing a nucleic acid to determine a genotype by performing a sequencing, hybridization, polymerization, or sequence specific endonuclease digestion reaction or by detecting the mass of the nucleic acid, or a portion thereof; or (ii) analyzing a polypeptide, or portion thereof, encoded by the nucleic acid by performing a sequencing, detection (e.g., ELISA), or sequence specific proteolytic digestion reaction, or by detecting the mass of the polypeptide, or a portion thereof.

As used herein, the terms "nucleic acid," "polynucleotide" and "oligonucleotide" refer to nucleic acid regions, nucleic acid segments, primers, probes, amplicons and oligomer fragments. The terms are not limited by length and are generic to linear polymers of polydeoxyribonucleotides (containing 2-deoxy-D-ribose), polyribonucleotides (containing D-ribose), and any other N-glycoside of a purine or pyrimidine base, or modified purine or pyrimidine bases. These terms include double- and single-stranded DNA, as well as double- and single-stranded RNA.

A nucleic acid, polynucleotide or oligonucleotide can comprise, for example, phosphodiester linkages or modified linkages including, but not limited to phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages.

A nucleic acid, polynucleotide or oligonucleotide can comprise the five biologically occurring bases (adenine, guanine, thymine, cytosine and uracil) and/or bases other than the five biologically occurring bases.

Optimal alignment of sequences for comparison may be conducted by the local homology algorithm of Smith and Waterman Add. APL. Math. 2:482 (1981), by the homology alignment algorithm of Needle man and Wunsch J. Mol.

Biol. 48:443 (1970), by the search for similarity method of Pearson and Lipman *Proc. Natl. Acad. Sci. (U.S.A.)* 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polypeptide sequences means that a polypeptide comprises a sequence that has at least 75% sequence identity. Alternatively, percent identity can be any integer from 75% to 100%. Exemplary embodiments include at least: 75%, 80%, 85%, 90%, 95%, or 99% compared to a reference sequence using the programs described herein; preferably BLAST using standard or default parameters, as described below. One of skill will recognize that these values can be appropriately adjusted to determine corresponding identity of proteins encoded by two nucleotide sequences by taking into account codon degeneracy, amino acid similarity, reading frame positioning and the like. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; a group of amino acids having acidic side chains is aspartic acid and glutamic acid; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine.

One indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C.

The term "promoter" or "regulatory element" refers to a region or sequence determinants located upstream or downstream from the start of transcription and which are involved in recognition and binding of RNA polymerase and other proteins to initiate transcription. Promoters need not be of plant origin, for example, promoters derived from plant viruses, such as the CaMV35S promoter, can be used.

The term "plant" includes whole plants, shoots, vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, seed tissue, ground tissue, and the like) and cells (e.g. guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous. In an exemplary embodiment, the plant is an oil palm plant (*E. guineensis* or *E. oleifera*, or a hybrid thereof). In some cases, the plant is *E. guineensis*.

An "expression cassette" refers to a nucleic acid construct, which when introduced into a host cell, results in transcription and/or translation of a RNA or polypeptide, respectively. Antisense constructs or sense constructs that are not or cannot be translated are expressly included by this definition. The expression cassette can contain a heterologous promoter.

The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

A polynucleotide sequence or amino acid sequence is "heterologous to" an organism or a second polynucleotide sequence if it originates from a foreign species, or, if from the same species, is modified from its original form. For example, a heterologous promoter operably linked to a coding sequence refers to a promoter from a species different from that from which the coding sequence was derived, or, if from the same species, a promoter that is different from any naturally occurring allelic variants, or a promoter that is not naturally found to be operably linked to the specified coding sequence in the specified plant.

As used herein, the term "nucleotide position" and the like, in the context of a nucleotide position of exon 1 of the SHELL gene refers to the position of a nucleotide relative to the adenosine of the wild-type SHELL gene initiator (i.e., amino terminal) methionine triplet codon ("ATG"). Thus, e.g., nucleotide position 1 refers to the adenosine of the ATG initator methionine triplet codon of the wild-type SHELL gene; and, position 2 refers to the next nucleotide (i.e., "T" of the ATG initiator methionine triplet codon), and so on. Similarly, in the context of a nucleotide position of intron 1 of the SHELL gene, the term "nucleotide position" and the like refers to the position of a nucleotide relative to the first nucleotide of intron 1 of the wild-type SHELL gene. Thus, the first nucleotide of intron 1 of the SHELL gene is at position 1, the second at position 2, and so on.

Similarly, the term "amino acid position" in the context of a particular amino acid, or group of amino acids, of the SHELL gene refers to an amino acid position relative to the initiator (i.e., amino terminal) methionine of the SHELL gene. Thus, for example, amino acid position 1 refers to the amino terminal methionine, amino acid position 2 refers to the adjacent glycine of the wild-type SHELL or an alternative amino acid or deletion found in a mutatnt SHELL allele at the same position. It will be appreciated that these positions are independent of any N-terminal degradation or conjugation or other post-translational processing. For example, in a SHELL polypeptide in which the N-terminal methionine amino acid is removed post-translationally, position 2 still refers to the previously adjacent glycine amino acid and position 3 refers to the adjacent arginine amino acid of the wild-type SHELL or an alternative amino acid or deletion found in a mutant SHELL allele at the same position.

DETAILED DESCRIPTION OF THE INVENTION

I. Introduction

Figure 1:
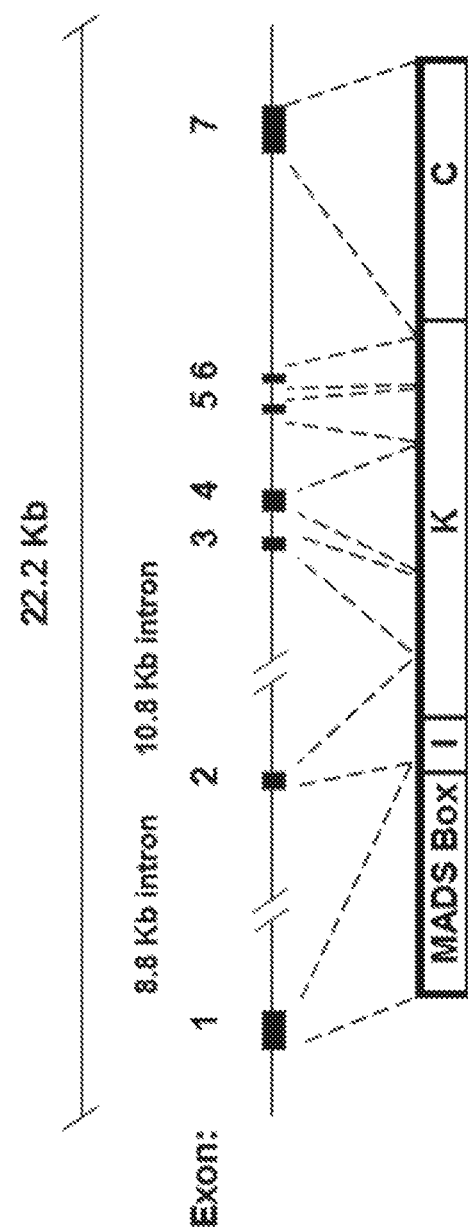
FIG. 1. SHELL gene model. Exons (boxes) and introns (horizontal lines) were validated by RNA-seq. A diagram of protein domains encoded by the indicated exons is provided below the gene diagram. MADS box, I, K and C domains of the SHELL protein are indicated.

The present disclosure describes the discovery of alleles 3-10 of the SHELL gene that are predicted to modulate the fruit form phenotype of palm (e.g., oil palm) plants. Similarly, alleles 11 (depicted in SEQ ID NOs: 11 and 21) and 12 (depicted in SEQ ID NO: 12) are either predicted to modulate the fruit form phenotype directly or can be used to infer the genotype of the SHELL gene due to their close physical linkage to the allele 3-10 polymorphisms. A polymorphic marker closely linked to the SHELL gene, or the identification of the presence, absence, or number of copies of alleles 3-11 in an oil palm plant can be used by seed producers as a quality control tool to i) reduce or eliminate *dura* or *pisifera* contamination of *tenera* seed or plantlets, ii) reduce or eliminate *dura* or *tenera* contamination of *pisifera* seed or plantlets, iii) reduce or eliminate *pisifera* or *tenera* contamination of *dura* seed or plantlets, iv) positively identify *tenera* seeds or plantlets which are then selected as suitable planting material for commercial palm oil production, v) positively identify *dura* seeds or plantlets which can then be selected as suitable planting material for commercial production of *dura* germplasm, or vi) positively identify *pisifera* seeds or plantlets which can then be selected as suitable planting material for commercial production of *pisifera* germplasm.

The identification of the SHELL gene or a marker genetically linked to shell trait is also of importance in breeding programmes. The marker or the alleles of the gene responsible for the trait can be used to separate the *dura, tenera* and *pisifera* plants in the nursery; the advantage here being that they could be planted separately based on shell fruit form phenotype. This is of interest as the *pisifera* palms usually show very vigorous vegetative growth, so in a trial consisting of all three types, distortion of results could occur due to intra-cross competition. Furthermore, separating out the *pisifera* palms and planting them in high density encourages male inflorescence and this facilitates pollen production which is used in breeding programmes (Jack et al., 1998). Accordingly, following detection of the presence or absence of a SHELL genotype predicted to result in a *dura, pisifera*, or *tenera* phenotype, or a linked marker as described below, a further step of: (1) reduction elimination of *dura* or *pisifera* contamination of *tenera* seed or plantlets, (2) positive identification of *tenera* seeds or plantlets which are then selected as suitable planting material for commercial palm oil production, or (3) separating *dura, tenera* and *pisifera* plants into two or more groups (e.g., plants predicted to be *tenera* in one group and plants predicted to be *dura* or *pisifera* in a second group; plants predicted to be *dura* in one group and plants predicted to be *tenera* or *pisifera* in a second group; plants predicted to be *pisifera* in one group and plants predicted to be *dura* or *tenera* in a second group, or separating into three groups: *dura, pisifera*, and *tenera*) can be achieved.

Any marker that exists that is polymorphic between the parent *dura* and *pisifera* trees in a cross and is linked to the shell locus has the potential to serve as a molecular signal to identify *tenera* trees in a cross. For example, if a *dura* tree, which is homozygous for "T" (i.e., T/T) at a given SNP position near the shell locus is crossed with a *pisifera* tree that is homozygous for "A" (i.e., A/A) at the same SNP position, then one could genotype seeds of the cross, or one could genotype plantlets arising from seeds of the cross, at the SNP position to track and identify contaminant seeds or plantlets. Seeds that are determined to be heterozygous at the SNP position, (i.e., A/T) are very likely to be *tenera*, unless a recombination between the marker and the shell gene had occurred in the individual being genotyped. Similarly, seeds which are homozygous at the SNP position for "A" or "T", (i.e., A/A or T/T), are *pisifera* or *dura* contaminant trees respectively, and when these trees become sexually mature in several years, they will produce suboptimal fruit types. Additionally, seeds or plantlets which have a "C" or "G" in the SNP position, neither of which is present in paternal palm of the cross, are likely trees arising from a different pollen donor than the one intended in the cross, and therefore can be discarded as contaminant seeds or plantlets. Markers that are in closer proximity to the SHELL locus would have higher predictive accuracy than markers that are farther away from the shell locus, because the closer the marker is to the shell gene, the less likely a recombination could occur which would break the linkage between the marker and the shell gene. Consequently, polymorphic markers within the shell gene itself are expected to have the strongest predictive power, and analysis of multiple markers closely linked to or within the shell gene may be advantageous.

II. Determination of Shell Phenotype Based on Nucleic Acid Detection

In view of the discovery that the SHELL genotype segregates with the *tenera/pisifera/dura* shell phenotype, genotyping a plant or seed at the SHELL locus or at adjacent genomic regions can be used to predict the shell phenotype of a palm plant.

SEQ ID NO:24 represents the predicted amino acid sequence of the N-terminal 181 amino acids of the protein expressed in oil palm of the *dura* fruit type ($Sh^{DeliDura}$). The endogenous protein includes additional C-terminal amino acids not included in SEQ ID NO:24. In oil palm of the *dura* fruit type, the proteins derived from both alleles of the gene include: (i) an isoleucine (I), lysine (K), arginine (R), isoleucine (I), and glutamate (E) at positions 8-12 respectively, which are deleted in predicted *pisifera* allele 7; (ii) a glutamate (E) at position 12, which is mutated to a glutamine (Q) in predicted *pisifera* allele 6; (iii) a lysine (K) at position 23 which is mutated to a glutamine (Q) in predicted *pisifera* allele 3 and an asparagine (N) in predicted *pisifera* allele 5; (iv) an arginine (R), which is mutated to a histidine (H) in predicted *pisifera* allele 8 and a glycine (G) in predicted *pisifera* allele 9; (v) a leucine (L) at position 29, which is mutated to a proline in the *pisifera* allele $sh^{MPOB}$; (vi) a lysine (K) at position 31, which is mutated to an asparagine in the *pisifera* allele $sh^{AVROS}$; (vii) a valine (V) at position 37, which is mutated to an aspartate (D) in predicted *pisifera* allele 10; and (viii) an alanine (A) at position 41, which is mutated to an aspartate (D) in predicted *pisifera* allele 4.

SEQ ID NO:1 represents the predicted amino acid sequence of the N-terminal 181 amino acids of the protein expressed in oil palm of the *pisifera* fruit type that is derived from the Zaire line ($sh^{AVROS}$). The endogenous protein includes additional C-terminal amino acids not included in SEQ ID NO: 1. This polypeptide includes an asparagine (N) amino acid at the $31^{st}$ amino acid position. A nucleotide sequence encoding exon 1 of the $sh^{AVROS}$ allele is provided in SEQ ID NO:22.

SEQ ID NO:2 represents the predicted amino acid sequence of the N-terminal 181 amino acids of the protein expressed in oil palm of the *pisifera* fruit type that is derived from the Nigerian line ($sh^{MPOB}$). The endogenous protein includes additional C-terminal amino acids not included here. This polypeptide includes a proline (P) amino acid at the $29^{th}$ amino acid position. A nucleotide sequence encoding exon 1 of the $sh^{MPOB}$ allele is provided in SEQ ID NO:23.

SEQ ID NO:3 represents the predicted amino acid sequence of the N-terminal 181 amino acids of the protein expressed in oil palm of the predicted *pisifera* fruit type SHELL allele 3. The endogenous protein includes additional C-terminal amino acids not included here. This polypeptide includes a glutamine (Q) amino acid at the $23^{rd}$ amino acid position. A nucleotide sequence encoding exon 1 of allele 3 is provided in SEQ ID NO: 13.

SEQ ID NO:4 represents the predicted amino acid sequence of the N-terminal 181 amino acids of the protein expressed in oil palm of the predicted *pisifera* fruit type SHELL allele 4. The endogenous protein includes additional C-terminal amino acids not included here. This polypeptide includes an aspartate (D) amino acid at the $41^{st}$ amino acid position. A nucleotide sequence encoding exon 1 of allele 4 is provided in SEQ ID NO: 14.

SEQ ID NO:5 represents the predicted amino acid sequence of the N-terminal 181 amino acids of the protein expressed in oil palm of the predicted *pisifera* fruit type SHELL allele 5. The endogenous protein includes additional C-terminal amino acids not included here. This polypeptide includes an asparagine (N) amino acid at the $23^{rd}$ amino acid position. A nucleotide sequence encoding exon 1 of allele 5 is provided in SEQ ID NO: 15.

SEQ ID NO:6 represents the predicted amino acid sequence of the N-terminal 181 amino acids of the protein expressed in oil palm of the predicted *pisifera* fruit type SHELL allele 6. The endogenous protein includes additional C-terminal amino acids not included here. This polypeptide includes a glutamine (E) amino acid at the $12^{th}$ amino acid position. A nucleotide sequence encoding exon 1 of allele 6 is provided in SEQ ID NO:16.

SEQ ID NO:7 represents the predicted amino acid sequence of the N-terminal 181 amino acids of the protein expressed in oil palm of the predicted *pisifera* fruit type SHELL allele 7. The endogenous protein includes additional C-terminal amino acids not included here. This polypeptide has a deletion of amino acids lysine (K), arginine (R), isoleucine (I), and glutamate (E), at positions 8-12 respectively in comparison to wildtype allele $Sh^{DeliDura}$. A nucleotide sequence encoding exon 1 of allele 7 is provided in SEQ ID NO: 17.

SEQ ID NO:8 represents the predicted amino acid sequence of the N-terminal 181 amino acids of the protein expressed in oil palm of the predicted *pisifera* fruit type SHELL allele 8. The endogenous protein includes additional C-terminal amino acids not included here. This polypeptide includes a histidine (H) amino acid at the $24^{th}$ amino acid position. A nucleotide sequence encoding exon 1 of allele 8 is provided in SEQ ID NO: 18.

SEQ ID NO:9 represents the predicted amino acid sequence of the N-terminal 181 amino acids of the protein expressed in oil palm of the predicted *pisifera* fruit type SHELL allele 9. The endogenous protein includes additional C-terminal amino acids not included here. This polypeptide includes a glycine (G) amino acid at the $24^{th}$ amino acid position. A nucleotide sequence encoding exon 1 of allele 9 is provided in SEQ ID NO: 19.

SEQ ID NO: 10 represents the predicted amino acid sequence of the N-terminal 181 amino acids of the protein expressed in oil palm of the predicted *pisifera* fruit type SHELL allele 10. The endogenous protein includes additional C-terminal amino acids not included here. This polypeptide includes an aspartate (D) amino acid at the $37^{th}$ amino acid position. A nucleotide sequence encoding exon 1 of allele 10 is provided in SEQ ID NO:20.

SEQ ID NO: 11 represents the predicted amino acid sequence of the N-terminal 181 amino acids of the protein expressed in oil palm of the predicted *pisifera* fruit type SHELL allele 11. The endogenous protein includes additional C-terminal amino acids not included here. The allele encodes a silent mutation with respect to a wild-type SHELL gene ($Sh^{DeliDura}$). A nucleotide sequence encoding exon 1 of allele 11 is provided in SEQ ID NO:21. As described herein, this silent mutation may affect transcriptional or translational regulation and therefore provide a *pisifera* phenotype despite encoding for a wild-type protein sequence. Alternatively, the nucleotide sequence encoding for this silent mutation can be used to infer the presence or absence of a genotype at one or more of the foregoing polymorphic nucleotide (e.g., one or more of the polymorphic markers relative to wild-type exemplified in SEQ ID Nos: 13-20, 13-20 and 23, 13-20 and 22, or 13-20 and 22-23) or amino acid markers (e.g., one or more of the polymorphic markers relative to wild-type exemplified in SEQ ID Nos: 3-10, 2-10, 1 and 3-10, or 1-10).

SEQ ID NO:12 represents the nucleotide sequence of the first 56 nucleotides of intron 1 of SHELL allele 12 in which nucleotides 43, 44, 45, and 46 are deleted relative to intron 1 of a wild-type SHELL allele ($Sh^{DeliDura}$). As this polymorphism is within a non-coding region of the SHELL gene, it is a silent mutation. As described herein, this silent mutation may affect transcriptional or translational regulation, or splicing, and therefore provide a *pisifera* phenotype. Alternatively, the presence or absence of allele 12 can be used to infer the presence or absence of a genotype at one or more of the foregoing polymorphic nucleotide (e.g., one or more of the polymorphic markers relative to wild-type exemplified in SEQ ID Nos: 13-20, 13-21, 13-20 and 22, 13-20 and 23, or 13-23) or amino acid markers (e.g., one or more of the polymorphic markers relative to wild-type exemplified in SEQ ID Nos: 3-10, 3-11, 2-10, 2-11, 1-10, 1 and 3-10, 1 and 3-11, or 1-11).

Oil palm trees of the *pisifera* fruit type are the result of one of at least four possibilities: i) two homozygous SHELL alleles having a nucleotide sequence coding for one of the following protein sequences: SEQ ID NOs:3-10; ii) two heterozygous SHELL alleles having two different nucleotide sequences independently coding for one of following protein sequences: SEQ ID NOs:3-10, or iii) one SHELL allele coding for the $Sh^{AVROS}$ or $Sh^{MPOB}$ protein sequence and the other allele coding for a mutation relative to wild-type represented in one or more of the following protein sequences: SEQ ID NOs:3-10. In some cases, nucleotide sequences comprising SEQ ID NO: 12 and/or 21 are similarly, predicted *pisifera* alleles. In such cases, a *pisifera* fruit type can result in plants homozygous for SEQ ID NO: 12 or 21 or heterozygous for SEQ ID NO: 12 or 21 and a different allele selected from the group consisting of any one of SEQ ID NOs:13-23 (e.g., any one of SEQ ID NOs:13-20) or encoding any one of SEQ ID NOs:1-10 (e.g., any one of SEQ ID NOs:3-10).

Oil palm trees of the *tenera* fruit type are the result of one allele coding for one or more of the *pisifera* alleles described herein and one allele coding for a wild-type ($Sh^{DeliDura}$) SHELL protein. It will be appreciated that SEQ ID NOs: 1-11 and 24 are representative sequences and that different individual palms may have an amino acid sequence having one, two, three, four, or more amino acid changes relative to SEQ ID NOS:1-11 and 24, due, for example, to natural variation. Similarly SEQ ID NOs: 12-23 and 25 are representative sequences and different individual palms may have a nucleotide sequence having one, two, three, four, or more nucleotide changes relative to SEQ ID NOs: 12-23 and 25 due to, for example, natural variation.

One or more polymorphism(s) between *pisifera* and *dura* SHELL alleles can be used to determine the shell phenotype of a palm or other plant. For example, when the polymorphism is co-dominant (detectable independent of the other allele) then:

the presence of only a *dura* SHELL allele indicates that the plant has or will have a *dura* shell phenotype;

the presence of only a *pisifera* SHELL allele indicates that the plant has or will have a *pisifera* shell phenotype; and the presence of a *pisifera* SHELL allele and a *dura* SHELL allele indicates that the plant has or will have a *tenera* shell phenotype.

However, genomic regions adjacent to the SHELL gene are also useful to determining whether a palm plant will likely manifest a particular shell phenotype. Because of genetic linkage to the SHELL gene, polymorphisms adjacent to the SHELL locus are predictive of shell phenotype, albeit with reduced accuracy as a function of increased distance from the SHELL locus. SEQ ID NO:27 provides an approximately 3.4 MB genomic region of the palm genome that comprises the SHELL gene. Table A of U.S. Patent Application Publication No. 2013/0247249 discloses 8217 SNPs identified within SEQ ID NO:27. A selection of these SNPs have been genetically mapped relative to the SHELL locus. The estimated predictive values of these SNPs are also described in Table A of U.S. 2013/0247249. Thus, as an example, the SNP listed in row 1 of U.S. 2013/0247249, Table A as having a estimated prediction success of 83, represents an SNP that is accurate in predicting shell phenotype 83% of the time. Said another way, by using this SNP as a genetic marker, one can correctly predict shell phenotype of palm plants 83 out of 100 times. Thus, even at a significant physical distance from the SHELL locus on the palm chromosome, polymorphic markers allow for relatively accurate prediction of shell phenotype of plants. In some embodiments, the polymorphic marker is within 1, 10, 20, 50, 100, 200, 500, 1000 kb from the SHELL gene (e.g., the gene corresponding to SEQ ID NO:28).

Accordingly, methods of detecting one or more polymorphic marker within a region of the palm genome corresponding to SEQ ID NO:27 are provided. Such methods are useful for predicting shell phenotype of palm plants for example. While over 8200 specific polymorphisms are provided in U.S. 2013/0247249, it should be appreciated that the polymorphisms represented are merely an example of polymorphisms within the genomic region corresponding to SEQ ID NO:27. Additional polymorphisms can be identified as desired and also be used to predict shell phenotype of a palm plant. Such additional polymorphisms are intended to be encompassed in the methods described herein. Moreover, it will be appreciated that SEQ ID NO:27 is a representative sequence and that different individual palms may have a corresponding genomic region having one or more nucleotide changes relative to SEQ ID NO:27 due, for example, to natural variation. As noted elsewhere herein, nevertheless, identifying the region of a genome corresponding to SEQ ID NO:27 can be readily determined using alignment programs, etc.

The nucleic acid sequences provided herein were generated by nucleotide sequencing and on occasion, include one or more stretches of "N's." These stretches of N's represent gaps in assembly of sequences of an estimated size. The precise number of N's in a sequence is an estimate (for example, 100 N's may only represent 30 bases). N's can be any base, and are likely repetitive sequence in the genome.

Detecting specific polymorphic markers can be accomplished by methods known in the art for detecting sequences at polymorphic sites. For example, standard techniques for genotyping for the presence of SNPs and/or microsatellite markers can be used, such as fluorescence-based techniques (Chen, X. et al., Genome Res. 9(5): 492-98 (1999)), utilizing PCR, LCR, Nested PCR and other techniques for nucleic acid amplification. Specific commercial methodologies available for SNP genotyping include, but are not limited to, TaqMan™ genotyping assays and SNPlex platforms (Applied Biosystems), gel electrophoresis (Applied Biosystems), mass spectrometry (e.g., MassARRAY system from Sequenom), minisequencing methods, real-time PCR, BioPlex system (BioRad), CEQ and SNPstream systems (Beckman), array hybridization technology (e.g., Affymetrix GeneChip; Perlegen), BeadArray Technologies (e.g., Illumina GoldenGate and Infinium assays), array tag technology (e.g., Parallele), and endonuclease-based fluorescence hybridization technology (Invader; Third Wave). Some of the available array platforms, including Affymetrix SNP Array 6.0 and Illumina CNV370-Duo and 1M BeadChips, include SNPs that tag certain copy number variants.

In certain embodiments, polymorphic markers are detected by sequencing technologies. Obtaining sequence information about an individual plant identifies particular nucleotides in the context of a sequence. For SNPs, sequence information about a single unique sequence site is sufficient to identify alleles at that particular SNP. For markers comprising more than one nucleotide, sequence information about the nucleotides of the individual that contain the polymorphic site identifies the alleles of the individual for the particular site.

Various methods for obtaining nucleic acid sequence are known to the skilled person, and all such methods are useful for practicing the invention. Sanger sequencing is a well-known method for generating nucleic acid sequence information. Recent methods for obtaining large amounts of sequence data have been developed, and such methods are also contemplated to be useful for obtaining sequence information of a plant, if desired. These include, but are not limited to, pyrosequencing technology (Ronaghi, M. et al. *Anal Biochem* 267:65-71 (1999); Ronaghi, et al., *Biotechniques* 25:876-878 (1998)), e.g., 454 pyrosequencing (Nyren, P., et al. *Anal Biochem* 208:171-175 (1993)), Illumina/Solexa sequencing technology (www.illumina.com; see also Strausberg, R L, et al *Drug Disc Today* 13:569-577 (2008)), Supported Oligonucleotide Ligation and Detection Platform (SOLiD) technology (Applied Biosystems, www.appliedbiosystems.com); Strausberg, R L, et al., *Drug Disc Today* 13:569-577 (2008), single-molecule, real-time sequencing (Pacific Biosciences), and IonTorrent technology (ThermoFisher).

Methods of polymorphism detection can be performed on any type of biological sample from the plant that contains nucleic acids (e.g., DNA, RNA). As one particular advantage of the methods is to predict the shell phenotype of young plants before cultivation in the field, in some embodiments, the samples are obtained from a plant that has been germinated less than 1, 2, 4, 6, months or less than 1, 2, 3, 4, or 5 years. In some embodiments, the plants are generated from i) a cross between *dura* and *pisifera* palms ii) the selfing of a *tenera* palm, iii) a cross between two plants having the *tenera* shell phenotype, iv) a cross between *dura* and *tenera* palms, and v) a cross between *tenera* and *pisifera* palms. Because such crosses are not 100% efficient, such crosses result in some percentage of seeds or plants that will not in the future produce seeds or plants with the *tenera* shell phenotype, (in case of i) and the observed number of *tenera* palms observed do not follow the expected Mendellian segregation (ii, iii & iv). By testing seeds or plants resulting from the attempted crosses, one can reduce or eliminate non-*tenera* contaminant seeds or plants from material planted for cultivation (optionally discarding those plants that are predicted to be *dura* and/or *pisifera*). Alternatively, one can identify and segregate plants based on their predicted shell genotype, allowing for selection and cultivation of fields of pure *pisifera* and *dura* trees, if desired, e.g., for later breeding purposes.

II. Transgenic Plants

As discussed above, the SHELL gene of palm has been discovered to control shell phenotype. Thus in some embodiments, plants having modulated expression of a SHELL polypeptide are provided. The more desirable shell phenotype (*tenera*, having a shell less than 2 mm thick) occurs naturally as a heterozygote of the between the *dura* and *pisifera* allele.

It has been discovered that *pisifera* SHELL alleles contain missense mutations in portions of the gene encoding the MADS box domain of the protein, which plays a role in transcription regulation. Thus, it is hypothesized that the *tenera* phenotype can result from a mechanism involving the protein:protein interaction of non-DNA binding *pisifera* types of SHELL proteins with fully functional types of SHELL (homodimers) or other MADS-box family members (heterodimers). Thus, in some embodiments, plants that heterologously express a SHELL polypeptide with a functional M, I, and K domain and a non-functional C-(MADs-box) domain are provided. M, I, K, and C domains are described in, e.g., Gramzow and Theissen, 2010 *Genome Biology* 11: 214-224 and the corresponding domains can be identified in the palm sequences described herein. By expressing such a protein having active protein:protein interaction domains but a non-functional DNA binding domain, proteins that interact with the modified SHELL protein will be removed from biological action, thereby resulting in a reduced shell thickness. Thus, for example, one can express any of the *pisifera* alleles described herein under control of a heterologous promoter in the plant (e.g., a palm plant, e.g., a *dura* background), thereby resulting in the reduced shell thickness.

Similarly, it has been discovered that many *pisifera* SHELL alleles contain mutations in a nuclear localization signal (NLS) within a MADS box domain of the SHELL protein. Thus, it is hypothesized that the *tenera* phenotype can result from a mechanism involving protein:protein interaction between one or more *pisifera* SHELL allele proteins lacking a functional NLS and one or more fully functional types of SHELL (homodimers) or other MADS-box family members (heterodimers). By expressing such a protein having active protein:protein interaction domains but a non-functional NLS, proteins that interact with the modified SHELL protein can be inhibited (e.g., prevented) from entering the nucleus or removed from the nucleus, thereby reducing the amount of biologically active SHELL protein and its interacting protein (e.g., binding partner) in the nucleus and resulting in a reduced shell thickness. Thus, for example, one can express any of the *pisifera* alleles containing an NLS mutation described herein, or a SHELL gene encoding a SHELL protein mutated at any of the (e.g., conserved) amino acids of the NLS under the control of a heterologous promoter in the plant (e.g., a palm plant, e.g., a *dura* background), thereby resulting in the reduced shell thickness.

B. Use of Nucleic Acids of the Invention to Enhance Gene Expression

Nucleic acid sequences encoding all or an active part of a SHELL polypeptide (including but not limited to polypeptides substantially identical to any one or more of SEQ ID NOs:1-10 (e.g., any one of SEQ ID NOs:3-10), SHELL polypeptides having a functional M, I, and K domain and a non-functional C domain, or SHELL polypeptides having a non-functional NLS, which when expressed control shell thickness) can be used to prepare expression cassettes that enhance, or increase SHELL gene expression. Where overexpression of a gene is desired, the desired SHELL gene from a different species may be used to decrease potential sense suppression effects.

Any of a number of means well known in the art can be used to increase SHELL activity in plants. Any organ can be targeted, such as shoot vegetative organs/structures (e.g.

leaves, stems and tubers), roots, flowers and floral organs/ structures (e.g. bracts, sepals, petals, stamens, carpels, anthers and ovules), seed (including embryo, endosperm, and seed coat) and fruit. Alternatively, a SHELL gene can be expressed constitutively (e.g., using the CaMV 35S promoter).

One of skill will recognize that the polypeptides encoded by the genes of the invention, like other proteins, have different domains which perform different functions. Thus, the gene sequences need not be full length, so long as the desired functional domain of the protein is expressed.

III. Preparation of Recombinant Vectors

In some embodiments, to use isolated sequences in the above techniques, recombinant DNA vectors suitable for transformation of plant cells are prepared. Techniques for transforming a wide variety of higher plant species are well known and described in the technical and scientific literature. See, for example, Weising et al. *Ann. Rev. Genet.* 22:421-477 (1988). A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, for overexpression, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumefaciens*, and other transcription initiation regions from various plant genes known to those of skill.

Alternatively, the plant promoter may direct expression of the polynucleotide of the invention in a specific tissue (tissue-specific promoters) or may be otherwise under more precise environmental control (inducible promoters). Examples of tissue-specific promoters under developmental control include promoters that initiate transcription only in certain tissues, such as fruit, seeds, or flowers. Examples of environmental conditions that may affect transcription by inducible promoters include anaerobic conditions, elevated temperature, or the presence of light.

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention can optionally comprise a marker gene that confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosluforon or Basta.

SHELL nucleic acid operably linked to a promoter is provided that, in some embodiments, is capable of driving the transcription of the SHELL coding sequence in plants. The promoter can be, e.g., derived from plant or viral sources. The promoter can be, e.g., constitutively active, inducible, or tissue specific. In construction of recombinant expression cassettes, vectors, transgenics, of the invention, a different promoters can be chosen and employed to differentially direct gene expression, e.g., in some or all tissues of a plant or animal. In some embodiments, as discussed above, desired promoters are identified by analyzing the 5' sequences of a genomic clone corresponding to a SHELL gene as described here.

V. Production of Transgenic Plants

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment. Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria.

Various palm transformation methods have been described. See, e.g., Masani and Parveez, *Electronic Journal of Biotechnology* Vol. 11 No. 3, Jul. 15, 2008; Chowdury et al., *Plant Cell Reports*, Volume 16, Number 5, 277-281 (1997).

Microinjection techniques are known in the art and well described in the scientific and patent literature. The introduction of DNA constructs using polyethylene glycol precipitation is described in Paszkowski et al. *EMBO J* 3:2717-2722 (1984). Electroporation techniques are described in Fromm et al. *Proc. Natl. Acad. Sci. USA* 82:5824 (1985). Ballistic transformation techniques are described in Klein et al. *Nature* 327:70-73 (1987).

*Agrobacterium tumefaciens*-mediated transformation techniques, including disarming and use of binary vectors, are well described in the scientific literature. See, for example Horsch et al. *Science* 233:496-498 (1984), and Fraley et al. *Proc. Natl. Acad. Sci. USA* 80:4803 (1983).

Transformed plant cells that are derived from any transformation technique can be cultured to regenerate a whole plant that possesses the transformed genotype and thus the desired phenotype. Such regeneration techniques rely on manipulation of certain phytohormones in a tissue culture growth medium, optionally relying on a biocide and/or herbicide marker that has been introduced together with the desired nucleotide sequences. Plant regeneration from cultured protoplasts is described in Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467-486 (1987).

The nucleic acids of the invention can be used to confer desired traits on essentially any plant. Thus, the invention has use over a broad range of plants, including species from the genera *Asparagus, Atropa, Avena, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malus, Manihot, Majorana, Medicago, Nicotiana, Oryza, Panieum, Pannesetum, Persea, Pisum, Pyrus, Prunus, Raphanus, Secale, Senecio, Sinapis, Solanum, Sorghum, Trigonella, Triticum, Vitis, Vigna,* and, *Zea.* Plants having a shell, and thus those that have use in the present invention, include but are not limited to dicotyledons and monocotyledons including but not limited to palm.

EXAMPLES

The following examples are offered to illustrate, but not to limit the claimed invention.

Example 1. Identification of Alleles 3-11, Corresponding to Nucleotide SEQ ID NOs:12-21 and Polypeptide SEQ ID NOs:3-11

We previously reported that the AVROS and MPOB mutations in exon 1 of the SHELL gene are responsible for the *pisifera* oil palm fruit form phenotype when homozygous (e.g., AVROS/AVROS, MPOB/MPOB or AVROS/MPOB) and the *tenera* oil palm fruit form phenotype when heterozygous along with one wildtype *dura* allele (e.g., AVROS/*dura* or MPOB/*dura*). While *tenera* oil palm is the preferred phenotype for commercial oil palm production, it is difficult to completely prevent the occurance of the wildtype *dura* palm in commercial populations. To estimate the degree of *dura* contamination within commercial oil palm populations, and to search for new alleles of the SHELL gene that are causative of the *pisifera/tenera* phenotype, we tested 5,158 oil palm trees from 6 different small holder plantations across Malaysia for the presence of the AVROS and/or MPOB alleles using an allele-specific PCR assay for each allele (*dura*, $sh^{AROS}$ and $sh^{MPOB}$). As expected, the majority of palms were heterozygous for either the $sh^{AVROS}$ or $sh^{MPOB}$ allele (Table 2).

However, 504 palms were predicted to be homozygous for the $Sh^{DeliDura}$ allele at both SNP positions. Exon 1 of the SHELL gene, encoding the entire MADS box domain, was sequenced in each of these 504 palms. Sequencing was performed on amplicons amplified by PCR using primers flanking exon 1. PCR was performed under standard conditions. Amplicons were purified and Sanger sequenced in one direction using a primer internal to the PCR amplification primers. Sequencing reads were individually analyzed within CONSED to determine the sequence and zygosity of each nucleotide position within exon 1. As shown in Table 2, 13 palms were determined to be heterozygous for the $sh^{AVROS}$ allele (2 from site 1, 4 from site 2, 2 from site 3, 3 from site 4 and 2 from site 5), indicating that these palms were indeed genotypically *tenera* palms. Three palms were determined to be heterozygous for the $sh^{MPOB}$ allele (1 from site 2, 1 from site 4 and 1 from site 5), indicating that these were also genotypically *tenera* palms. However, the remaining 488 palms were homozygous for the $Sh^{DeliDura}$ allele at both SNP positions, suggesting these trees were genotypically *dura* or that they carried previously unidentified mutant alleles of the SHELL gene.

Figure 3:
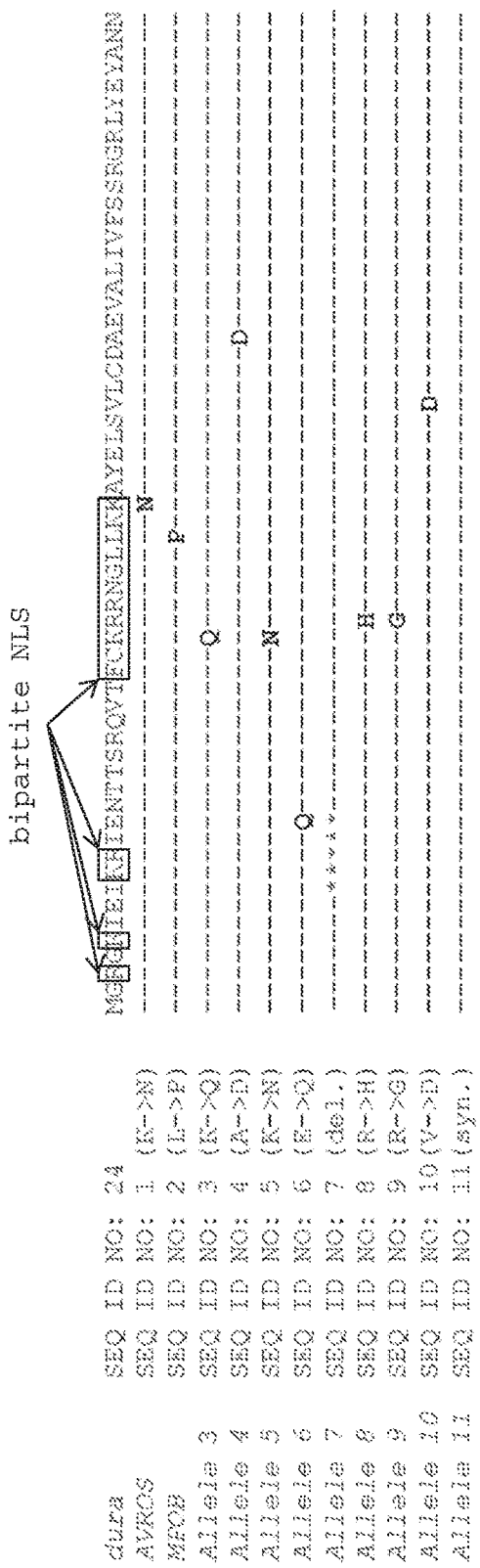
FIG. 3. Amino acid variants in the SHELL gene. The peptide sequence of the wildtype ($Sh^{DeliDura}$) MADS box domain (SEQ ID NO: 24) is shown in the top line of the peptide alignment. Sequences of the AVROS, MPOB, Allele 3, Allele 4, Allele 5, Allele 6, Allele 7, Allele 8, Allele 9, Allele 10 and Allele 11 (SEQ ID NO: 1-11, respectively) peptides are shown aligned to the *dura* peptide sequence. Variant amino acids caused by missense single nucleotide variants are indicated by the appropriate single letter amino acid code. Deleted amino acids (Allele 7) are indicated by astericks. Amino acids that are unchanged relative to *dura* peptide sequence are indicated by dashes.

Allele 3 (SEQ ID NO: 3 and 13) was found to be heterozygous in 68 palms (Table 2), Allele 4 (SEQ ID NO: 4 and 14) was found to be heterozygous in 66 palms and Allele 5 was found to be heterozygous in 1 palm. Each of these 135 palms were independent of each other. The amino acids encoded by Alleles 3 and 5 occur within the NLS of SHELL, as do the AVROS and MPOB mutations (FIG. 3). The amino acid encoded by Allele 4 lies 10 amino acids C-terminal to the amino acid mutated by the $sh^{AVROS}$ allele.

TABLE 2

Determination of SHELL exon 1 genotypes in palms sampled from small holder plantations.

| Small Holder Plantation Site | Tested[a] | Sequenced[b] | AVROS | MPOB | Allele 3 | Allele 4 | Allele 5 | Allele 6 | Allele 7 | Allele 8 | Allele 9 | Allele 10 | Allele 11 |
|---|---|---|---|---|---|---|---|---|---|---|---|---|---|
| 1 | 940 | 102 | 2 | — | 1 | 23 | 1 | — | — | — | — | — | — |
| 2 | 1,133 | 126 | 4 | 1 | — | 16 | — | — | — | — | — | — | — |
| 3 | 720 | 27 | 2 | — | — | 4 | — | — | — | — | — | — | — |
| 4 | 1,092 | 36 | 3 | 1 | — | 11 | — | — | — | — | — | — | — |
| 5 | 922 | 145 | 2 | 1 | 58 | 11 | — | — | — | — | — | — | — |
| 6 | 351 | 68 | — | — | 9 | 1 | — | — | — | — | — | — | — |

[a]Number of independent palms tested for AVROS and MPOB mutations by allele specific PCR assays
[b]Nubmer of independent palms further analyzed by DNA sequencing of exon 1 of the SHELL gene Next, we genotyped 3,952 palms from seven oil palm nursery sites throughout Malaysia (Table 3). Again, the majority were heterozygous for either the shAVROS or shMPOB allele, indicated that they were genotypically *tenera* palms. However, 536 palms were predicted to be homozygous for the $Sh^{DeliDura}$ allele at both SNP positions. Exon 1 of the SHELL gene, encoding the entire MADS box domain, was sequenced in each of these 536 palms as described above.

As shown in Table 3, 6 palms were determined to be heterozygous for the $sh^{AVROS}$ allele, indicating that these palms were indeed genotypically *tenera* palms. One palm was determined to be heterozygous for the $sh^{MPOB}$ allele. However, the remaining 529 palms were determined to be homozygous for the $Sh^{DeliDura}$ allele at both SNP positions, suggesting these trees were genotypically *dura* or that they carried previously unidentified mutant alleles of the SHELL gene. Allele 3 (SEQ ID NO: 3 and 13) was found to be heterozygous in 36 palms (Table 3), and Allele 4 (SEQ ID NO: 4 and 14) was found to be heterozygous in 2 palms. Each of these 38 palms were independent of each other.

TABLE 3

Determination of SHELL exon 1 genotypes in palms sampled from oil palm nurseries.

| Nursery Site | Tested[a] | Sequenced[b] | AVROS | MPOB | Allele 3 | Allele 4 | Allele 5 | Allele 6 | Allele 7 | Allele 8 | Allele 9 | Allele 10 | Allele 11 |
|---|---|---|---|---|---|---|---|---|---|---|---|---|---|
| 1 | 539 | 40 | 1 | — | 1 | — | — | — | — | — | — | — | — |
| 2 | 571 | 134 | — | 1 | 18 | — | — | — | — | — | — | — | — |
| 3 | 576 | 147 | 2 | — | 12 | 2 | — | — | — | — | — | — | — |

TABLE 3-continued

Determination of SHELL exon 1 genotypes in palms sampled from oil palm nurseries.

| Nursery Site | Tested[a] | Sequenced[b] | AVROS | MPOB | Allele 3 | Allele 4 | Allele 5 | Allele 6 | Allele 7 | Allele 8 | Allele 9 | Allele 10 | Allele 11 |
|---|---|---|---|---|---|---|---|---|---|---|---|---|---|
| 4 | 571 | 94 | — | — | 5 | — | — | — | — | — | — | — | — |
| 5 | 550 | 22 | 1 | — | — | — | — | — | — | — | — | — | — |
| 6 | 572 | 65 | — | — | — | — | — | — | — | — | — | — | — |
| 7 | 573 | 34 | 2 | — | — | — | — | — | — | — | — | — | — |

[a]Number of independent palms tested for AVROS and MPOB mutations by allele specific PCR assays
[b]Nubmer of independent palms further analyzed by DNA sequencing of exon 1 of the SHELL gene To further identify SHELL exon 1 variants, we sequenced exon 1 of the SHELL gene in 148 palms from germplasm collections collected from various geographical regions (64 from Angola, 28 from Ghana, 27 from Nigeria, 27 from Tanzania and 2 from Guinea). The sh$^{AVROS}$ allele was most common among populations expected to be of the *tenera* phenotype (50 Angola, 10 Ghana, 6 Nigeria, and 22 Nigeria palms), while the sh$^{MPOB}$ allele was detected in 5 Angola, 5 Ghana and 19 Nigeria palms (Table 4). Allele 4 (also detected in small holder plantations and nurseries) was detected in 1 Ghana and 2 Guinea palms.

Figure 2:
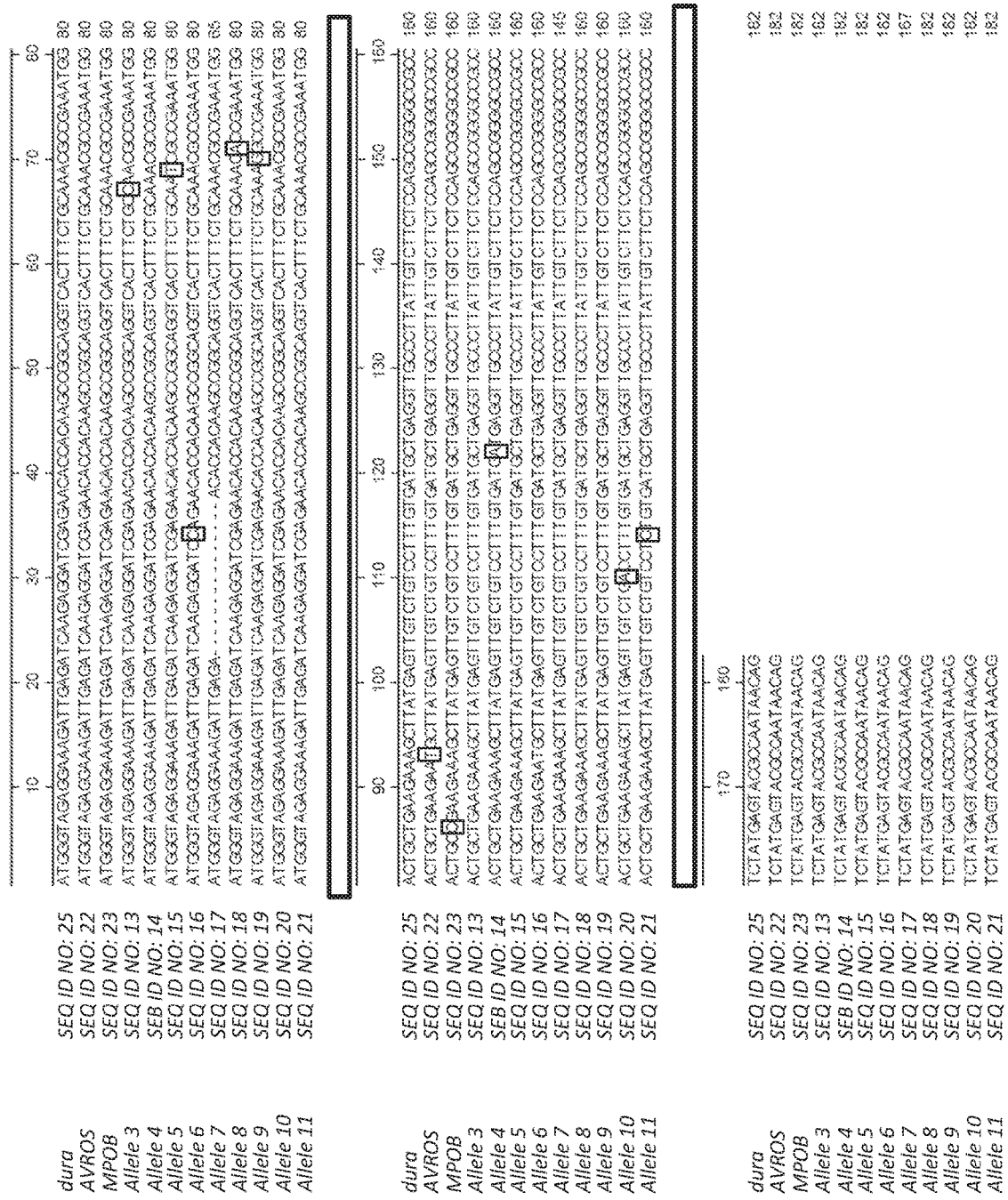
FIG. 2. Nucleotide variants in the SHELL gene. The DNA sequence of the wildtype ($Sh^{DeliDura}$) exon 1 encoding the MADS box domain of SHELL (SEQ ID NO: 25) is shown in the top line of the DNA sequence alignment. Sequences of the AVROS, MPOB, Allele 3, Allele 4, Allele 5, Allele 6, Allele 7, Allele 8, Allele 9, Allele 10 and Allele 11 (SEQ ID NO: 22, 23, 13-21, respectively) alleles are shown aligned to the *dura* sequence. Single nucleotide variants are indicated by boxes. Deleted bases (Allele 7) are indicated by dashes.

In addition, six novel SHELL alleles were detected. Allele 6 was detected in 4 Tanzania palms and encodes an aspartate to glutamine amino acid change relative to *dura* at amino acid position 12 (FIGS. 2 and 3). Allele 7, an inframe deletion removing 5 amino acids relative to *dura* was detected in 1 Nigeria palm. Alleles 8 and 9 alter the same amino acid relative to *dura*. The conserved arginine at amino acid position 24 is changed to histidine in Allele 8 and to glycine in Allele 9 (FIGS. 2 and 3). Allele 10 was detected in one Ghana palm, and it encodes a valine to glutamate amino acid substitution relative to *dura* at amino acid position 37. Finally, Allele 11 was detected in two Angola palms, and it encodes a synonomous single nucleotide polymorphism (FIG. 2). It is noteworthy that, like sh$^{AVROS}$ and sh$^{MPOB}$ mutations, Alleles 3, 5, 7, 8 and 9 all affect amino acids that are part of the highly conserved NLS of the SHELL protein.

Of 10 Ghana palms phenotyped as *tenera*, 1 was heterozygous for Allele 4 (Allele 4/Sh$^{DeliDura}$) and was wildtype (*dura*) at all other exon 1 nucleotide positions, 4 were heterozygous for Allele 8 (Allele 8/Sh$^{DeliDura}$) and were wildtype (*dura*) at all other exon 1 nucleotide positions, 4 were heterozygous for Allele 9 (Allele 9/Sh$^{DeliDura}$) and were wildtype (*dura*) at all other exon 1 nucleotide positions, and 1 was heterozygous for Allele 10 (Allele 10/Sh$^{DeliDura}$) and was wildtype (*dura*) at all other exon 1 nucleotide positions. None of the Ghana palms in this study were phenotyped as *dura*.

Of 8 Nigeria palms phenotyped as *tenera*, 3 were heterozygous for the sh$^{AVROS}$ allele (sh$^{AVROS}$/Sh$^{DeliDura}$) and wildtype (*dura*) at all other nucleotide positions, 3 were heterozygous for the sh$^{MPOB}$ allele (sh$^{MPOB}$/Sh$^{DeliDura}$) and wildtype (*dura*) at all other exon 1 nucleotide positions, and 1 was heterozygous for Allele 7 (Allele 7/Sh$^{DeliDura}$) and wildtype (*dura*) at all other exon 1 nucleotide positions. One Nigeria palm phenotyped as *tenera* was wildtype (*dura*) at all exon 1 nucleotide positions. Of two Nigeria palms phenotyped as *pisifera*, 1 was homozygous for the sh$^{AVROS}$ allele and was wildtype (*dura*) at all other exon 1 nucleotide positions, while the other was heterozygous for the sh$^{AVROS}$ allele (sh$^{AVROS}$/Sh$^{DeliDura}$) and was wildtype (*dura*) at all other exon 1 nucleotide positions. None of the Nigeria palms in this study were phenotyped as *dura*.

Of 2 Tanzania palms phenotyped as *tenera*, 1 was heterozygous for sh$^{AVROS}$ allele (sh$^{AVROS}$/Sh$^{DeliDura}$) and was

TABLE 4

Determination of SHELL exon 1 genotypes in germplasm collections.

| | Sequenced | AVROS | MPOB | Allele 3 | Allele 4 | Allele 5 | Allele 6 | Allele 7 | Allele 8 | Allele 9 | Allele 10 | Allele 11 |
|---|---|---|---|---|---|---|---|---|---|---|---|---|
| Angola | 64 | 50 | 5 | — | — | — | — | — | — | — | — | 2 |
| Ghana | 28 | 10 | 5 | — | 1 | — | — | — | 4 | 4 | 1 | — |
| Nigeria | 27 | 6 | 19 | — | — | — | — | 1 | — | — | — | — |
| Tanzania | 27 | 22 | — | — | — | — | 4 | — | — | — | — | — |
| Guinea | 2 | — | — | — | 2 | — | — | — | — | — | — | — |

Among the palms sequenced as part of the germplasm collection, 32 were visually phenotyped for oil palm fruit type (*dura*, *tenera* or *pisifera*). Of three Angola palms phenotyped as *tenera*, two were heterozygous for the sh$^{AVROS}$ allele and were wildtype (*dura*) at all other exon 1 nucleotide positions within exon 1. Of two Angola palms phenotyped as *dura*, both were heterozygous for the Allele 11 variant (Allele 11/Sh$^{DeliDura}$) and were wildtype (*dura*) at all other exon 1 nucleotide positions, consistent with the expectation that the synonymous change is not directly involved in the *tenera/pisifera* phenotype. One Angola palm phenotyped as *tenera* was wildtype (*dura*) at all exon 1 nucleotide positions. None of the Angola palms in this study were phenotyped as *pisifera*.

wildtype (*dura*) at all other exon 1 nucleotide positions, while the other was a compound heterzygote with the shAVROS allele on one chromosome and Allele 6 on the other chromosome (sh$^{AVROS}$/Allele 6) and was wildtype (*dura*) at all other exon 1 nucleotide positions. Furthermore, 3 of 3 Tanzania palms phenotyped as *dura* were heterozygous for Allele 6. This suggests that although Allele 6 may not contribute to the *tenera* phenotype, it may be a marker for closely linked alleles that do contribute to the phenotype. No Tanzania palms in this study were phenotyped as *pisifera*.

Of 2 Guinea palms phenotyped as *tenera*, 1 was heterozygous for Allele 4 (Allele 4/Sh$^{DeliDura}$) and was wildtype (*dura*) at all other exon 1 nucleotide positions. The other was homozygous for Allele 4 and was wildtype (*dura*) at all other exon 1 nucleotide positions. None of Guinea palms in this study were phenotyped as *dura* or *pisifera*.

REFERENCES

Beimaert, A. and Vanderweyen, R. 1941. Contribution a l'etude genetique et biometrique des varieties *d'Elaeis guineensis* Jacq. Publs. INEAC, Series Ser. Sci. (27):101.

Bhasker, S. & Mohankumar, C. Association of lignifying enzymes in shell synthesis of oil palm fruit (*Elaeis guineensis—dura* variety). 2001. *Indian J Exp Biol* 39: 160-4.

Billotte, N., Marseillac, N., Risterucci, A. M., Adon, B., Brotteir, P., Baurens, F. C., Singh, R., Herran, A., Asmady, H., Billot, C., Amblard, P Durrand-Gasselin, T., Courtois, B., Asmono, D., Cheah, S. C., Rohde, W and Charrier, A. 2005. Microsatellite-based high density linkage map in oil palm (*Elaeis guineensis* Jacq.). Theoretical and Applied Genetics 110: 754-765.

Birchler, J. A., Auger, D. L. & Riddle, N. C. 2003. In search of the molecular basis of heterosis. *Plant Cell* 15: 2236-9.

Cheah, S. C. 1996. Restriction Fragment Length Polymorphism (RFLP) in Oil Palm. Project Completion Report No. 0011/95, 4 Jul. 1996, Malaysian Palm Oil Board (MPOB), Bangi, Malaysia.

Cheah, S. C. and Rajinder, S. 1998. Gene expression during flower development in the oil palm. Project Completion Report No. 0057/98, 16 Jul. 1999. Palm Oil Research Institute of Malaysia (PORIM), Bangi, Malaysia.

Corley, R. H. V. and Tinker, P. B. 2003. Care and maintenance of oil palms. In *The Oil Palm* (4$^{th}$ edition), pp:287-326. Oxford: Blackwell Science.

Danielsen, F. et al. 2009. Biofuel plantations on forested lands: double jeopardy for biodiversity and climate. *Conserv Biol* 23: 348-58.

Devuyst, A. 1953. Selection of the oil palm (*Elaeis guineensis*) in Africa. *Nature* 172: 685-686.

Dinneny, J. R. and Yanofsky, M. F. 2005. Drawing lines and borders: how the dehiscent fruit of *Arabidopsis* is patterned. *Bioessays* 27: 42-9.

Donough, C. R. and Law, I. H. 1995. Breeding and selection for seed production at Pamol Plantations Sdn Bhd and early performance of Pamol D×P. *Planter* 71:513-530.

Doyle, J. J. and Doyle, J. L. 1990. Isolation of plant DNA from fresh tissue. *FOCUS* 12:13-15.

Ferrandiz, C., Liljegren, S. J. & Yanofsky, M. F. 2000. Negative regulation of the SHATTERPROOF genes by FRUITFULL during *Arabidopsis* fruit development. *Science* 289: 436-8.

Godding, R. 1930. Observation de la production de palmiers selectionnes a Mongana (Equateur). *Bull Arig. Congo belge* 21: 1263.

Gschwend, M. et al. 1996. A locus for Fanconi anemia on 16q determined by homozygosity mapping. *Am J Hum Genet* 59: 377-84.

Gu, Q., Ferrandiz, C., Yanofsky, M. F. & Martienssen, R. 1998. The FRUITFULL MADS-box gene mediates cell differentiation during *Arabidopsis* fruit development. *Development* 125: 1509-17.

Gramzow, L. and Theissen, G. 2010. A hitchhiker's guide to the MADS world of plants. *Genome Biology* 11: 214-225.

Hardon, J. J., Rao, V., and Rajanaidu, N. 1985. A review of oil palm breeding. In Progress in Plant Breeding, ed G. E. Rusell, pp 139-163, Butterworths, UK.

Hartley, C. W. S. 1988. The botany of oil palm. In *The oil palm* (3$^{rd}$ edition), pp:47-94, Longman, London.

Huang, H., Tudor, M., Su, T., Zhang, Y., Hu, Y., and Ma, H. 1996. DNA binding properties of two *Arabidopsis* MADS domain proteins: Binding Consensus and Dimer Formation. *The Plant Cell* 8: 81-94.

Imminck, R. G., Gadella, T. W. J., Ferrario, S., Busscher, M., and Angenent, G. 2002. *Proc. Natl. Acad. Sci.* 99: 2416-2421.

Imminck, R. G., Kaufmann, K. & Angenent, G. C. 2010. The 'ABC' of MADS domain protein behaviour and interactions. *Semin Cell Dev Biol* 21: 87-93.

Jack, P. L., James, C., Price, Z., Rance, K., Groves, L., CorleY, R. H. V., Nelson, S and Rao, V. 1998. Application of DNA markers in oil palm breeding. In: 1998 International Oil Palm Congress-Commodity of the past, today and future, Sep. 23-25, 1998, Bali, Indonesia.

Krieger, U., Lippman, Z. B. & Zamir, D. 2010. The flowering gene SINGLE FLOWER TRUSS drives heterosis for yield in tomato. *Nat Genet* 42: 459-63.

Lander, E. S. and Botstein, D. 1987. Homozygosity mapping: a way to map human recessive traits with the DNA of inbred children. *Science* 236: 1567-70.

Latiff, A. 2000. The Biology of the Genus *Elaeis*. In: *Advances in Oil Palm Research,* Volume 1, ed. Y. Basiron, B. S. Jalani, and K. W. Chan, pp:19-38, Malaysian Palm Oil Board (MPOB).

Liljegren, S. J., Ditta, G. S., Eshed, Y., Savidge, B., Bowman, J. L., Yanofsky, M. F. 2000. SHATTERPROOF MADS-box genes control seed dispersal in *Arabidopsis*. *Nature* 404: 766-770.

Maria, M., Clyde, M. M. and Cheah, S. C. 1995. Cytological analysis of *Elaeis guineensis* (*tenera*) chromosomes. *Elaeis* 7:122-134.

Mayes, S., Jack, P. L., Marshall, D. F. and Corley, R. H. V. 1997. Construction of a RFLP genetic linkage map for oil palm (*Elaeis guineensis* Jacq.). *Genome* 40:116-122.

Moretzsohn, M. C., Nunes, C. D. M., Ferreira, M. E. and Grattapaglia, D. 2000. RAPD linkage mapping of the shell thickness locus in oil palm (*Elaeis guineensis* Jacq.). *Theoretical and Applied Genetics* 100:63-70.

Ooijen, J. W. V. 2006. JoinMap 4.0: Software for calculation of genetic linkage maps. In experimental populations. Kyazma B. V., Wageningen, Netherlands Pinyopich, A. et al. 2003. Assessing the redundancy of MADS-box genes during carpel and ovule development. *Nature* 424: 85-8.

Purseglove, J. W. 1972. Tropical Crops. Monocotyledons. Longman, London. pp:607.

Rajanaidu, N., Rao, V., Abdul Halim, H. & A. S. H., O. 1989. Genetic resources: New developments in Oil Palm breeding. *Elaeis* 1: 1-10.

Rajanaidu, N. 1990. Major developments in oil palm (*Elaeis guineensis*) breeding. In Proceedings of the 12$^{th}$ Plenary Meeting of AETFAT, pp: 39-52. Hamburg, Germany.

Rajanaidu, N. et al. 2000. in *Advances in Oil Palm Research* (eds. Basiron, Y., Jalani, B. S. & Chan, K. W.) 171-237 (Malaysian Palm Oil Board (MPOB), Bangi, Selangor).

Sambrook, J., Fritsch, E. F. and Maniatis, T. 1989. Molecular cloning: A Laboratory manual, (2$^{nd}$ edition). Cold Spring Harbor Laboratory Press, Cold Spring Harbor, N.Y.

Singh R, Tan S G, Panandam J M, Rahman R A, Ooi L C L, Low E T L, Sharma M, Jansen J and Cheah S C. 2009. Mapping quantitative trait loci (QTLs) for fatty acid composition in an interspecific cross of oil palm. *BMC Plant Biology* 9: 114.

Sousa, J., Barata, A. V., Sousa, C., Casanova, C. C. and Vicente, L. 2011. Chimpanzee oil-palm use in southern Cantanhez National Park, Guinea-Bissau. *Am J Primatol* 73: 485-97.

Tani, E., Polidoros, A. N. & Tsaftaris, A. S. Characterization and expression analysis of FRUITFULL- and SHATTERPROOF-like genes from peach (*Prunus persica*) and their role in split-pit formation. 2007. *Tree Physiol* 27: 649-59.

Vrebalov, J., Pan, I. L., Arroyo, A. J. M., McQuinn, R., Chung, M., Poole, M., Rose, J., Seymour, G., Grandillo, S., Giovannoni, J., and Irish, V. F. 2009. Fleshy fruit expansion and ripening are regulated by the tomato SHATTERPROOF gene TAGL1. *The Plant Cell* 21: 3041-3062.

Whitmore, T. C. 1973. The Palms of Malaya. Longmans, Malaysia, pp:56-58.

The term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety.

```
INFORMAL LISTING OF EXEMPLARY SEQUENCES
SHELL predicted protein sequence, mutation
underlined, italicized, and bold [pisifera,
Zaire allele; sh^AVROS]
                                       SEQ ID NO: 1
MGRGKIEIKRIENTTSRQVTFCKRRNGLLKNAYELSVLCDAEVALIVFSS

RGRLYEYANNSIRSTIDRYKKACANSSNSGATIEINSQYYQQESAKLRHQ

IQILQNANRHLMGEALSTLTVKELKQLENRLERGITRIRSKKHELLFAEI

EYMQKREVELQNDNMYLRAKIAENERAQQAA

SHELL predicted protein sequence mutation
underlined, italicized, and bold [pisifera,
Nigerian allele; sh^MPOB]
                                       SEQ ID NO: 2
MGRGKIEIKRIENTTSRQVTFCKRRNGLPKKAYELSVLCDAEVALIVFSS

RGRLYEYANNSIRSTIDRYKKACANSSNSGATIEINSQYYQQESAKLRHQ

IQILQNANRHLMGEALSTLTVKELKQLENRLERGITRIRSKKHELLFAEI

EYMQKREVELQNDNMYLRAKIAENERAQQAA

SHELL predicted protein sequence mutation
underlined, italicized, and bold [predicted
pisifera, Allele 3]
                                       SEQ ID NO: 3
MGRGKIEIKRIENTTSRQVTFCQRRNGLLKKAYELSVLCDAEVALIVFSS

RGRLYEYANNSIRSTIDRYKKACANSSNSGATIEINSQYYQQESAKLRHQ

IQILQNANRHLMGEALSTLTVKELKQLENRLERGITRIRSKKHELLFAEI

EYMQKREVELQNDNMYLRAKIAENERAQQAA

SHELL predicted protein sequence mutation
underlined, italicized, and bold [predicted
pisifera, Allele 4]
                                       SEQ ID NO: 4
MGRGKIEIKRIENTTSRQVTFCKRRNGLLKKAYELSVLCDDEVALIVFSS

RGRLYEYANNSIRSTIDRYKKACANSSNSGATIEINSQYYQQESAKLRHQ

IQILQNANRHLMGEALSTLTVKELKQLENRLERGITRIRSKKHELLFAEI

EYMQKREVELQNDNMYLRAKIAENERAQQAA

SHELL predicted protein sequence mutation
underlined, italicized, and bold [predicted
pisifera, Allele 5]
                                       SEQ ID NO: 5
MGRGKIEIKRIENTTSRQVTFCNRRNGLLKKAYELSVLCDAEVALIVFSS

RGRLYEYANNSIRSTIDRYKKACANSSNSGATIEINSQYYQQESAKLRHQ

IQILQNANRHLMGEALSTLTVKELKQLENRLERGITRIRSKKHELLFAEI

EYMQKREVELQNDNMYLRAKIAENERAQQAA

SHELL predicted protein sequence mutation
underlined, italicized, and bold [predicted
pisifera, Allele 6]
                                       SEQ ID NO: 6
MGRGKIEIKRIQNTTSRQVTFCKRRNGLLKKAYELSVLCDAEVALIVFSS

RGRLYEYANNSIRSTIDRYKKACANSSNSGATIEINSQYYQQESAKLRHQ

IQILQNANRHLMGEALSTLTVKELKQLENRLERGITRIRSKKHELLFAEI

EYMQKREVELQNDNMYLRAKIAENERAQQAA

SHELL predicted protein sequence deleted amino
acids indicated by a dash ("-") [predicted
pisifera, Allele 7]
                                       SEQ ID NO: 7
MGRGKIE-----NTTSRQVTFCKRRNGLLKKAYELSVLCDAEVALIVFSS

RGRLYEYANNSIRSTIDRYKKACANSSNSGATIEINSQYYQQESAKLRHQ

IQILQNANRHLMGEALSTLTVKELKQLENRLERGITRIRSKKHELLFAEI

EYMQKREVELQNDNMYLRAKIAENERAQQAA

SHELL predicted protein sequence mutation
underlined, italicized, and bold [predicted
pisifera, Allele 8]
                                       SEQ ID NO: 8
MGRGKIEIKRIENTTSRQVTFCKHRNGLLKKAYELSVLCDAEVALIVFSS

RGRLYEYANNSIRSTIDRYKKACANSSNSGATIEINSQYYQQESAKLRHQ

IQILQNANRHLMGEALSTLTVKELKQLENRLERGITRIRSKKHELLFAEI

EYMQKREVELQNDNMYLRAKIAENERAQQAA

SHELL predicted protein sequence mutation
underlined, italicized, and bold [predicted
pisifera, Allele 9]
                                       SEQ ID NO: 9
MGRGKIEIKRIENTTSRQVTFCKGRNGLLKKAYELSVLCDAEVALIVFSS

RGRLYEYANNSIRSTIDRYKKACANSSNSGATIEINSQYYQQESAKLRHQ

IQILQNANRHLMGEALSTLTVKELKQLENRLERGITRIRSKKHELLFAEI

EYMQKREVELQNDNMYLRAKIAENERAQQAA

SHELL predicted protein sequence mutation
underlined, italicized, and bold [predicted
pisifera, Allele 10]
                                       SEQ ID NO: 10
MGRGKIEIKRIENTTSRQVTFCKRRNGLLKKAYELSDLCDAEVALIVFSS

RGRLYEYANNSIRSTIDRYKKACANSSNSGATIEINSQYYQQESAKLRHQ

IQILQNANRHLMGEALSTLTVKELKQLENRLERGITRIRSKKHELLFAEI

EYMQKREVELQNDNMYLRAKIAENERAQQAA

SHELL predicted protein sequence, silent mutation
results in wildtype amino acid sequence [predicted
pisifera, Allele 11]
                                       SEQ ID NO: 11
MGRGKIEIKRIENTTSRQVTFCKRRNGLLKKAYELSVLCDAEVALIVFSS

RGRLYEYANNSIRSTIDRYKKACANSSNSGATIEINSQYYQQESAKLRHQ
```

IQILQNANRHLMGEALSTLTVKELKQLENRLERGITRIRSKKHELLFAEI

EYMQKREVELQNDNMYLRAKIAENERAQQAA

Deletion in intron 1 of SHELL gene, deleted
nucleotides in reference to wild-type denoted with
a dash ("-")

SEQ ID NO: 12
GTATGCTTTGATGACGCCTTCTCTTCCTTCGCTCATATCAAG----

TTTTATGGCTTCA T

SHELL Exon 1 Sequence of Allele 3, mutation
underlined, italicized, and bold

SEQ ID NO: 13
ATGGGTAGAGGAAAGATTGAGATCAAGAGGATCGAGAACACCACAAGCCG

GCAGGTCACTTTCTGC*C*AACGCCGAAATGGACTGCTGAAGAAAGCTTATG

AGTTGTCTGTCCTTTGTGATGCTGAGGTTGCCCTTATTGTCTTCTCCAGC

CGGGGCCGCCTCTATGAGTACGCCAATAACAG

SHELL Exon 1 Sequence of Allele 4, mutation
underlined, italicized, and bold

SEQ ID NO: 14
ATGGGTAGAGGAAAGATTGAGATCAAGAGGATCGAGAACACCACAAGCCG

GCAGGTCACTTTCTGCAAACGCCGAAATGGACTGCTGAAGAAAGCTTATG

AGTTGTCTGTCCTTTGTGATG*A*TGAGGTTGCCCTTATTGTCTTCTCCAGC

CGGGGCCGCCTCTATGAGTACGCCAATAACAG

SHELL Exon 1 Sequence of Allele 5, mutation
underlined, italicized, and bold

SEQ ID NO: 15
ATGGGTAGAGGAAAGATTGAGATCAAGAGGATCGAGAACACCACAAGCCG

GCAGGTCACTTTCTGCAA*T*CGCCGAAATGGACTGCTGAAGAAAGCTTATG

AGTTGTCTGTCCTTTGTGATGCTGAGGTTGCCCTTATTGTCTTCTCCAGC

CGGGGCCGCCTCTATGAGTACGCCAATAACAG

SHELL Exon 1 Sequence of Allele 6, mutation
underlined, italicized, and bold

SEQ ID NO: 16
ATGGGTAGAGGAAAGATTGAGATCAAGAGGATC*C*AGAACACCACAAGCCG

GCAGGTCACTTTCTGCAAACGCCGAAATGGACTGCTGAAGAAAGCTTATG

AGTTGTCTGTCCTTTGTGATGCTGAGGTTGCCCTTATTGTCTTCTCCAGC

CGGGGCCGCCTCTATGAGTACGCCAATAACAG

SHELL Exon 1 Sequence of Allele 7, deleted
nucleotides in reference to wild-type denoted
by a dash ("-")

SEQ ID NO: 17
ATGGGTAGAGGAAAGATTGAGA---------------ACACCACAAGCCG

GCAGGTCACTTTCTGCAAACGCCGAAATGGACTGCTGAAGAAAGCTTATG

AGTTGTCTGTCCTTTGTGATGCTGAGGTTGCCCTTATTGTCTTCTCCAGC

CGGGGCCGCCTCTATGAGTACGCCAATAACAG

SHELL Exon 1 Sequence of Allele 8, mutation
underlined, italicized, and bold

SEQ ID NO: 18
ATGGGTAGAGGAAAGATTGAGATCAAGAGGATCGAGAACACCACAAGCCG

GCAGGTCACTTTCTGCAAA*C*ACCGAAATGGACTGCTGAAGAAAGCTTATG

AGTTGTCTGTCCTTTGTGATGCTGAGGTTGCCCTTATTGTCTTCTCCAGC

CGGGGCCGCCTCTATGAGTACGCCAATAACAG

SHELL Exon 1 Sequence of Allele 9, mutation
underlined, italicized, and bold

SEQ ID NO: 19
ATGGGTAGAGGAAAGATTGAGATCAAGAGGATCGAGAACACCACAAGCCG

GCAGGTCACTTTCTGCAAA*G*GCCGAAATGGACTGCTGAAGAAAGCTTATG

AGTTGTCTGTCCTTTGTGATGCTGAGGTTGCCCTTATTGTCTTCTCCAGC

CGGGGCCGCCTCTATGAGTACGCCAATAACAG

SHELL Exon 1 Sequence of Allele 10, mutation
underlined, italicized, and bold

SEQ ID NO: 20
ATGGGTAGAGGAAAGATTGAGATCAAGAGGATCGAGAACACCACAAGCCG

GCAGGTCACTTTCTGCAAACGCCGAAATGGACTGCTGAAGAAAGCTTATG

AGTTGTCTG*A*CCTTTGTGATGCTGAGGTTGCCCTTATTGTCTTCTCCAGC

CGGGGCCGCCTCTATGAGTACGCCAATAACAG

SHELL Exon 1 Sequence of Allele 11, mutation
underlined, italicized, and bold

SEQ ID NO: 21
ATGGGTAGAGGAAAGATTGAGATCAAGAGGATCGAGAACACCACAAGCCG

GCAGGTCACTTTCTGCAAACGCCGAAATGGACTGCTGAAGAAAGCTTATG

AGTTGTCTGTCCT*C*TGTGATGCTGAGGTTGCCCTTATTGTCTTCTCCAGC

CGGGGCCGCCTCTATGAGTACGCCAATAACAG

SHELL Exon 1 Sequence of sh$^{AVROS}$ Allele, mutation
underlined, italicized, and bold

SEQ ID NO: 22
ATGGGTAGAGGAAAGATTGAGATCAAGAGGATCGAGAACACCACAAGCCG

GCAGGTCACTTTCTGCAAACGCCGAAATGGACTGCTGAAGAA*T*GCTTATG

AGTTGTCTGTCCTTTGTGATGCTGAGGTTGCCCTTATTGTCTTCTCCAGC

CGGGGCCGCCTCTATGAGTACGCCAATAACAG

SHELL Exon 1 Sequence of sh$^{MPOB}$ Allele, mutation
underlined, italicized, and bold

SEQ ID NO: 23
ATGGGTAGAGGAAAGATTGAGATCAAGAGGATCGAGAACACCACAAGCCG

GCAGGTCACTTTCTGCAAACGCCGAAATGGACTGC*C*GAAGAAAGCTTATG

AGTTGTCTGTCCTTTGTGATGCTGAGGTTGCCCTTATTGTCTTCTCCAGC

CGGGGCCGCCTCTATGAGTACGCCAATAACAG

Wild-type SHELL (Sh$^{DeliDura}$) predicted protein
sequence. Amino acids mutated in sh$^{AVROS}$, sh$^{MPOB}$,
and alleles 3-6 and 8-10 are underlined,
italicized, and bold. Amino acids mutated in
allele 7 are underlined.
[dura, Sh$^{DeliDura}$]

SEQ ID NO: 24
MGRGKIEIKRIENTTSRQVTFCKRRNGLLKKAYELSVICDAE

VALIVFSSRGRLYEYANNSIRSTIDRYKKACANSSNSGATIEINSQYYQQE

SAKLRHQIQILQNANRHLMGEALSTLTVKELKQLENRLERGITRIRSKKHE

LLFAEIEYMQKREVELQNDNMYLRAKIAENERAQQAA

Wild-type SHELL (Sh$^{DeliDura}$) Exon 1 Sequence,
nucleotides mutated in sh$^{AVROS}$, sh$^{MPOB}$, and
alleles 3-6 and 8-11 are underlined, italicized,
and bold. Nucleotides deleted in allele 7 are
underlined

SEQ ID NO: 25
ATGGGTAGAGGAAAGATTGAGA*TCAAGAGGATCG*AGAACACCACAAGCCG

GCAGGTCACTTTCTGC*AAACG*CCGAAATGGACTGC*T*GAAGAA*A*GCT

-continued

```
TATGAGTTGTCTGTCCTTTGTGATGCTGAGGTTGCCCTTATTGTCTT

CTCCAGCCGGGGCCGCCTCTATGAGTACGCCAATAACAG

Wild-type SHELL (Sh^DeliDura) Exon 1 merged with
nucleotides 1-119 of intron 1
                                       SEQ ID NO: 26
ATGGGTAGAGGAAAGATTGAGATCAAGAGGATCGAGAACACCACAAGCCG

GCAGGTCACTTTCTGCAAACGCCGAAATGGACTGCTGAAGAAAGCTTATG
```

-continued

```
AGTTGTCTGTCCTTTGTGATGCTGAGGTTGCCCTTATTGTCTTCTCCAGC

CGGGGCCGCCTCTATGAGTACGCCAATAACAGGTATGCTTTGATGACGCC

TTCTCTTCCTTCGCTCATATCAAGTTAATTTTATGGCTTCATTTGTTCTA

TGGCCAAGCCAAATTCTTTTTAAAGTTCTAGAATGTTAATGATGGTAGTT

T
```

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US10905061B2). An electronic copy of the "Sequence Listing" will also be available from the USPTO upon request and payment of the fee set forth in 37 CFR 1.19(b)(3).

What is claimed is:

1. A method for segregating a plurality of *Elaeis guineensis* (*E. guineensis*) palm plants or seeds into different categories based on predicted shell phenotype, the method comprising:
   (a) predicting the shell phenotype of the palm plants or seeds based on the presence, absence, or number of *pisifera* or *dura* alleles by:
      (i) obtaining the genotype of nucleotide 67 of exon 1 of the SHELL gene, wherein a A to C mutation of nucleotide 67 of exon 1 of the SHELL gene indicates the presence of a *pisifera* allele; or
      (ii) obtaining the genotype of nucleotide 69 of exon 1 of the SHELL gene, wherein a A to T mutation of nucleotide 69 of exon 1 of the SHELL gene indicates the presence of a *pisifera* allele; or
      (iii) obtaining the genotype of nucleotide 70 of exon 1 of the SHELL gene, wherein a C to G mutation of nucleotide 70 of exon 1 of the SHELL gene indicates the presence of a *pisifera* allele; or
      (iv) obtaining the genotype of nucleotide 71 of exon 1 of the SHELL gene, wherein an G to A mutation of nucleotide 71 of exon 1 of the SHELL gene indicates the presence of a *pisifera* allele; or
      (v) obtaining the genotype of nucleotide 110 of exon 1 of the SHELL gene, wherein an T to A mutation of nucleotide 110 of exon 1 of the SHELL gene indicates the presence of a *pisifera* allele; or
      (vi) obtaining the genotype of nucleotide 122 of exon 1 of the SHELL gene, wherein an C to A mutation of nucleotide 122 of exon 1 of the SHELL gene indicates the presence of a *pisifera* allele; or
      (vii) obtaining the genotype of nucleotides 23-37 of exon 1 of the SHELL gene, wherein a 15 base pair deletion mutation corresponding to nucleotides 23-37 of exon 1 of the SHELL gene and causing an in frame deletion of five amino acids at positions 8 to 12 in the translated open reading frame of exon 1, indicates the presence of a *pisifera* allele; and
   (b) segregating the plants or seeds into groups based on the genotype of the nucleotide(s), wherein at least one group only contains one of (i) plants or seeds predicted to have a *tenera* shell phenotype, (ii) plants or seeds predicted to have the *dura* shell phenotype, or (iii) plants or seeds predicted to have the *pisifera* shell phenotype, wherein the presence of one predicted *pisifera* allele and one predicted *dura* allele predicts the *tenera* shell phenotype, wherein the *pisifera* shell phenotype comprises homozygosity of the mutant allele at the nucleotide, or wherein the *dura* shell phenotype comprises homozygosity of the wild-type allele at the nucleotide.

2. The method of claim 1, wherein the palm plants or seeds are generated from (i) an attempted cross between a plant having the *dura* shell phenotype and a plant having the *pisifera* shell phenotype, (ii) selfing of a *tenera* palm, (iii) a cross between two plants having the *tenera* shell phenotype, (iv) a cross between *dura* and *tenera* palms, or (v) a cross between *tenera* and *pisifera* palms.

3. The method of claim 1, wherein the palm plants are less than 5 years old.

4. The method of claim 1, wherein the palm plants or seeds are discarded if the palm plants or seeds do not have a genotype predictive of the *tenera* shell phenotype.

5. The method of claim 1, wherein determining the presence, absence, or number of *pisifera* or *dura* alleles comprises obtaining the genotype of the polymorphic marker corresponding to nucleotide 122 of exon 1 of the SHELL gene, and wherein a mutation relative to wild type of the polymorphic marker indicates the presence of a *pisifera* allele, wherein a C to A mutation of the polymorphic marker corresponding to nucleotide 122 of exon 1 of the SHELL gene indicates the presence of a *pisifera* allele.

6. The method of claim 1, wherein determining the presence, absence, or number of *pisifera* or *dura* alleles comprises obtaining the genotype of nucleotide 34 of exon 1 of the SHELL gene, wherein a G to C mutation of nucleotide 34 of exon 1 of the SHELL gene indicates the presence of a *pisifera* allele.

7. The method of claim 1, wherein the obtaining the genotype of the nucleotide(s) comprises detecting the genotype of the nucleotide(s) by sequencing.

8. The method of claim 7, wherein the presence, absence, or number of *pisifera* or *dura* alleles is determined by detecting SEQ ID NO: 13, SEQ ID NO: 14, SEQ ID NO: 15, SEQ ID NO: 17, SEQ ID NO: 18, SEQ ID NO: 19 or SEQ ID NO: 20.

9. The method of claim 1, further comprising selecting plants or seeds for cultivation if the plants or seeds have a genotype predictive of the *tenera* shell phenotype.

10. The method of claim 1, further comprising selecting plants or seeds for cultivation if the plants or seeds have a genotype predictive of the *dura* shell phenotype.

11. The method of claim 1, further comprising selecting plants or seeds for cultivation if the plants or seeds have a genotype predictive of the *pisifera* shell phenotype.

12. The method of claim 1, wherein the predicting comprises obtaining the genotype of nucleotide 67 of exon 1 of the SHELL gene, wherein an A to C mutation of nucleotide 67 of exon 1 of the SHELL gene indicates the presence of a *pisifera* allele.

13. The method of claim 1, wherein the predicting comprises obtaining the genotype of nucleotide 69 of exon 1 of the SHELL gene, wherein an A to T mutation of nucleotide 69 of exon 1 of the SHELL gene indicates the presence of a *pisifera* allele.

14. The method of claim 1, wherein the predicting comprises obtaining the genotype of nucleotide 70 of exon 1 of the SHELL gene, wherein an C to G mutation of nucleotide 70 of exon 1 of the SHELL gene indicates the presence of a *pisifera* allele.

15. The method of claim 1, wherein the predicting comprises obtaining the genotype of nucleotide 71 of exon 1 of the SHELL gene, wherein an G to A mutation of nucleotide 71 of exon 1 of the SHELL gene indicates the presence of a *pisifera* allele.

16. The method of claim 1, wherein the predicting comprises obtaining the genotype of nucleotide 110 of exon 1 of the SHELL gene, wherein an T to A mutation of nucleotide 110 of exon 1 of the SHELL gene indicates the presence of a *pisifera* allele.

17. The method of claim 1, wherein the predicting comprises obtaining the genotype of nucleotide 122 of exon 1 of the SHELL gene, wherein an C to A mutation of nucleotide 122 of exon 1 of the SHELL gene indicates the presence of a *pisifera* allele.

18. The method of claim 1, wherein the predicting comprises obtaining the genotype of nucleotides 23-37 of exon 1 of the SHELL gene, wherein an C to A mutation of nucleotides 23-37 of exon 1 of the SHELL gene in causing an in frame deletion of five amino acids at positions 8 to 12 of the translated open reading frame of exon 1, indicates the presence of a *pisifera* allele.

\* \* \* \* \*